(12) United States Patent
Jeong et al.

(10) Patent No.: US 9,968,343 B2
(45) Date of Patent: May 15, 2018

(54) MINIMALLY INVASIVE SURGICAL INSTRUMENT HAVING A BENT SHAFT

(76) Inventors: Chang Wook Jeong, Seoul (KR); Hyung Tae Kim, Incheon (KR)

(*) Notice: Subject to any disclaimer, the term of this patent is extended or adjusted under 35 U.S.C. 154(b) by 966 days.

(21) Appl. No.: 14/007,299

(22) PCT Filed: Mar. 23, 2012

(86) PCT No.: PCT/KR2012/002148
§ 371 (c)(1),
(2), (4) Date: Dec. 11, 2013

(87) PCT Pub. No.: WO2012/128591
PCT Pub. Date: Sep. 27, 2012

(65) Prior Publication Data
US 2014/0114293 A1    Apr. 24, 2014

(30) Foreign Application Priority Data

Mar. 24, 2011    (KR) .................. 10-2011-0026243

(51) Int. Cl.
*A61B 17/00*    (2006.01)
*A61B 17/29*    (2006.01)
(Continued)

(52) U.S. Cl.
CPC ........ *A61B 17/00234* (2013.01); *A61B 17/29* (2013.01); *A61B 34/70* (2016.02);
(Continued)

(58) Field of Classification Search
CPC ... A61B 17/00234; A61B 17/29; A61B 34/70; A61B 34/71; A61B 2034/306;
(Continued)

(56) References Cited

U.S. PATENT DOCUMENTS 6,817,974 B2* 11/2004 Cooper ............ A61B 17/00234
600/142
8,398,633 B2*  3/2013 Mueller ................ A61B 17/29
606/51
(Continued)

FOREIGN PATENT DOCUMENTS

KR    10-2010-0132560    12/2010

OTHER PUBLICATIONS

Korean Intellectual Property Office, International search report for International Application No. PCT/KR2012/002148, dated Oct. 25, 2012.

*Primary Examiner* — David C Eastwood
*Assistant Examiner* — Vynn Huh
(74) *Attorney, Agent, or Firm* — Dinsmore & Shohl LLP

(57) ABSTRACT

The present invention relates to a minimally invasive surgical instrument having a bent shaft, and more particularly to a minimally invasive surgical instrument in which at least a part of a shaft includes a bend. According to one aspect of the invention, there is provided a minimally invasive surgical instrument comprising: a shaft; an end effector connected to one end of the shaft; a joint unit interposed between the shaft and the end effector; and a plurality of wires connected to the joint unit to enable the end effector to carry out joint motion, wherein the shaft comprises at least one bend, and the at least one bend may transmit therein force to operate the end effector in a roll direction, independently of the shaft.

The present invention relates to a minimally invasive surgical instrument having a bent shaft, and more particularly, to a minimally invasive surgical instrument in which at least a portion of a shaft is curved. A minimally invasive surgical instrument according to one embodiment of the present invention comprises: a shaft; an end effector connected to one end of the shaft; an articulation unit interposed between (Continued)

the shaft and the end effector; and a plurality of wires connected to the articulation unit so as to enable the end effector to move in an articulating manner. The shaft has at least one curve, and said at least one curve is capable of independently transmitting force to the inside of the end effector such that the end effector may operate in a rolling direction.

10 Claims, 20 Drawing Sheets

(51) Int. Cl.
*A61B 34/00* (2016.01)
*A61B 34/30* (2016.01)

(52) U.S. Cl.
CPC .... *A61B 34/71* (2016.02); *A61B 2017/00309* (2013.01); *A61B 2017/00314* (2013.01); *A61B 2017/00323* (2013.01); *A61B 2017/00738* (2013.01); *A61B 2017/291* (2013.01); *A61B 2017/2904* (2013.01); *A61B 2017/2908* (2013.01); *A61B 2017/2927* (2013.01); *A61B 2017/2929* (2013.01); *A61B 2034/306* (2016.02)

(58) Field of Classification Search
CPC ........... A61B 2017/00309; A61B 2017/00314; A61B 2017/00323; A61B 2017/00738; A61B 2017/2904; A61B 2017/291; A61B 2017/2927; A61B 2017/2929
See application file for complete search history.

(56) References Cited

U.S. PATENT DOCUMENTS

| | | | |
|---|---|---|---|
| 9,033,998 B1* | 5/2015 | Schaible | A61B 17/00234 606/130 |
| 2007/0282371 A1* | 12/2007 | Lee | A61B 17/062 606/205 |
| 2008/0039255 A1 | 2/2008 | Jinno et al. | |
| 2008/0119871 A1* | 5/2008 | Brock | A61B 17/0469 606/130 |
| 2010/0087818 A1* | 4/2010 | Cunningham | A61B 17/29 606/53 |
| 2010/0234831 A1 | 9/2010 | Hinman et al. | |

\* cited by examiner

[Fig. 1]
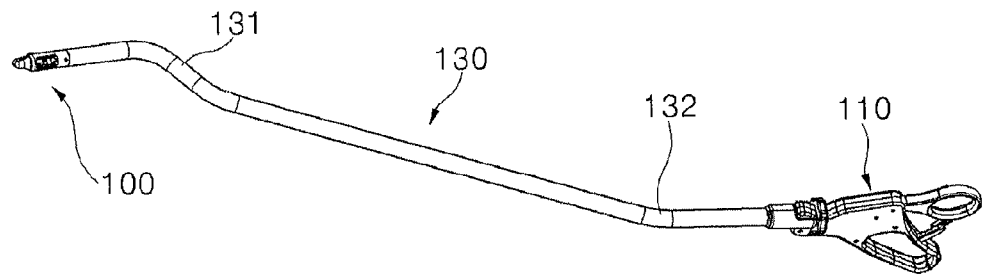
[Fig. 2]
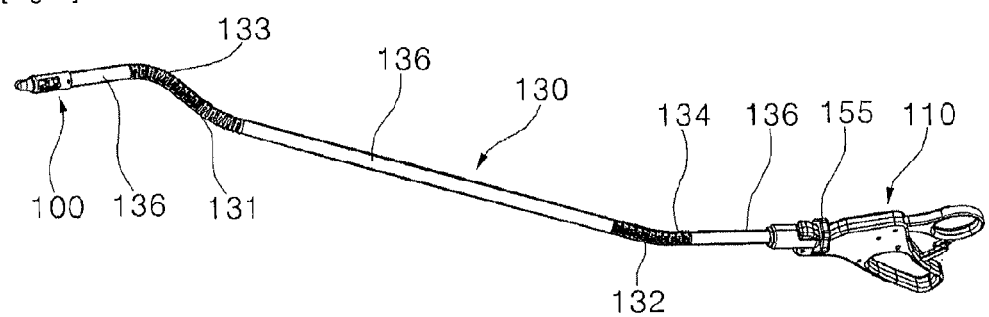
[Fig. 3]
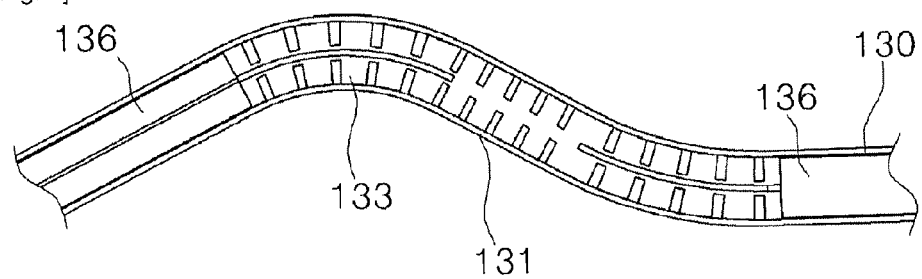
[Fig. 4]
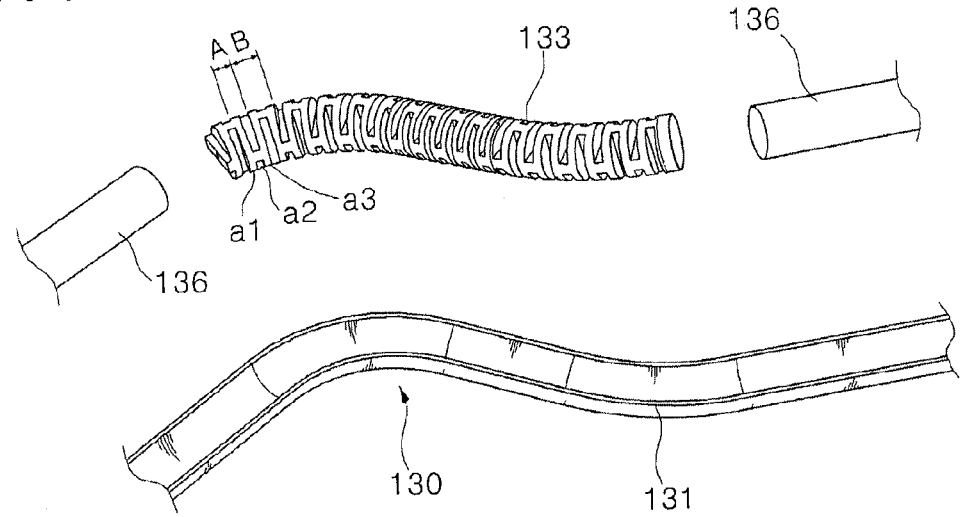

[Fig. 5]
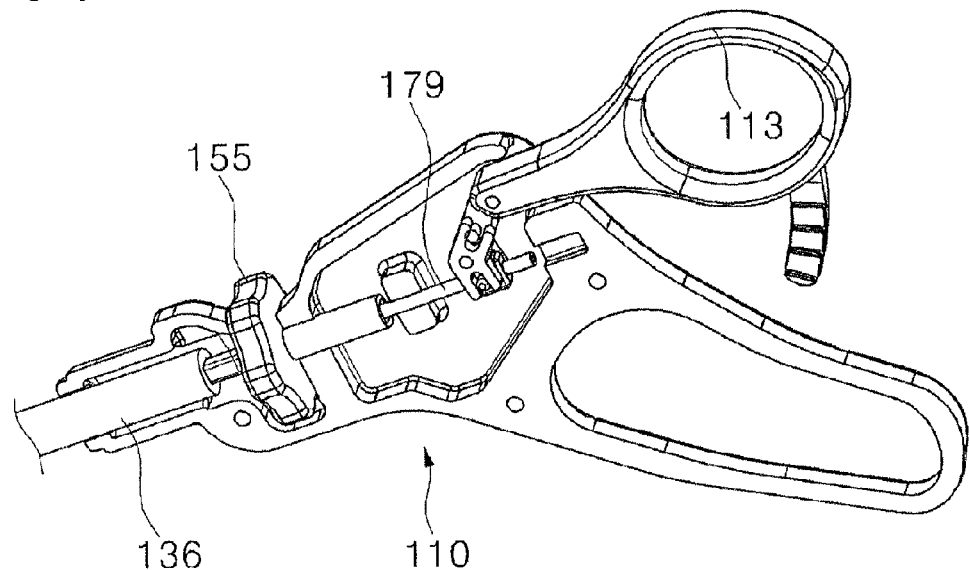
[Fig. 6]
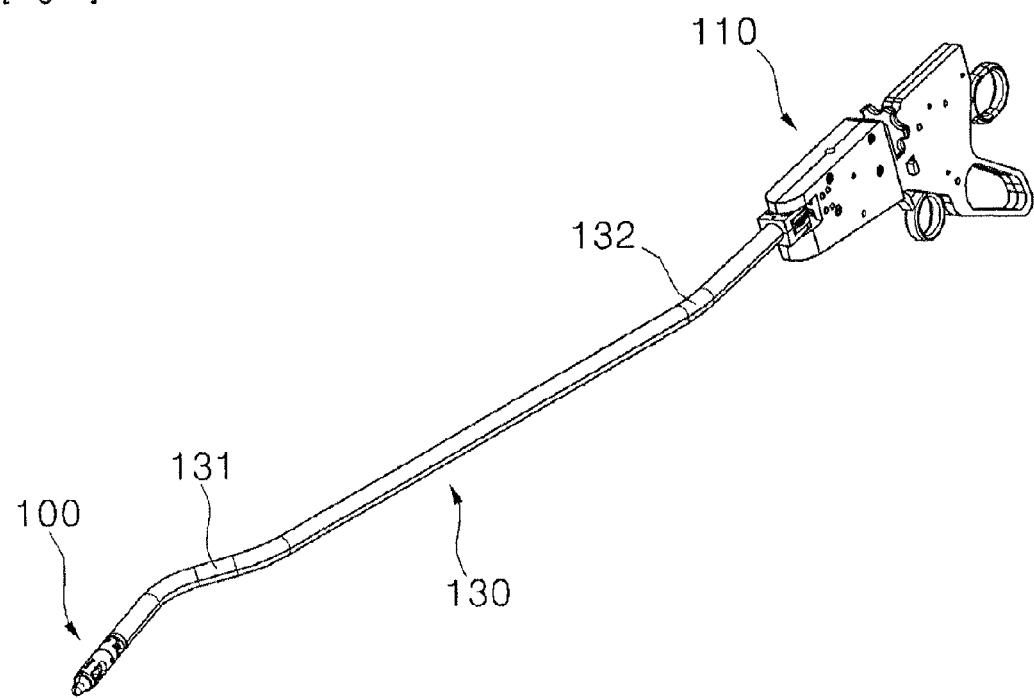

[Fig. 7]
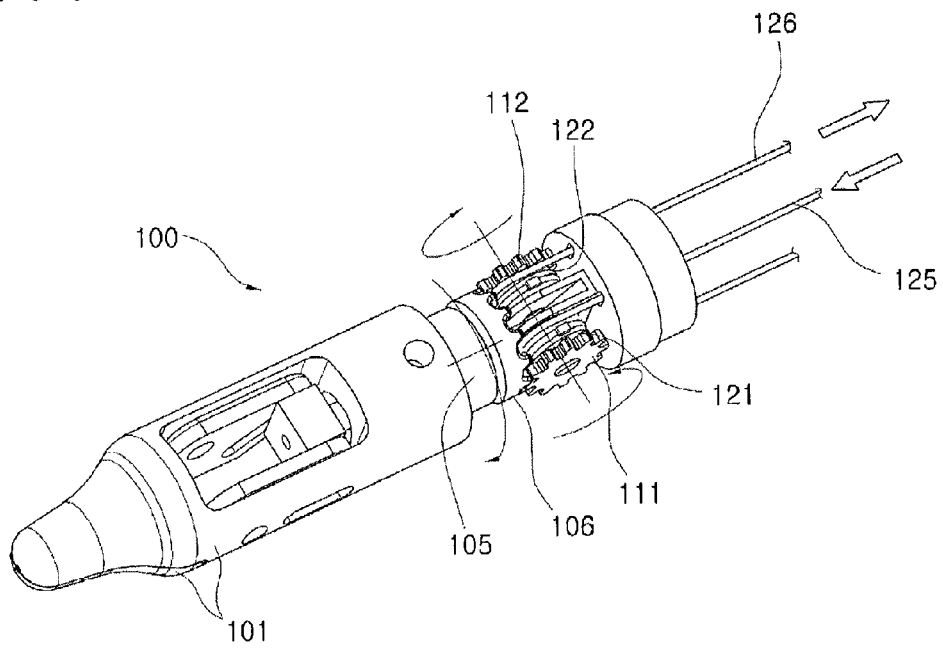
[Fig. 8]
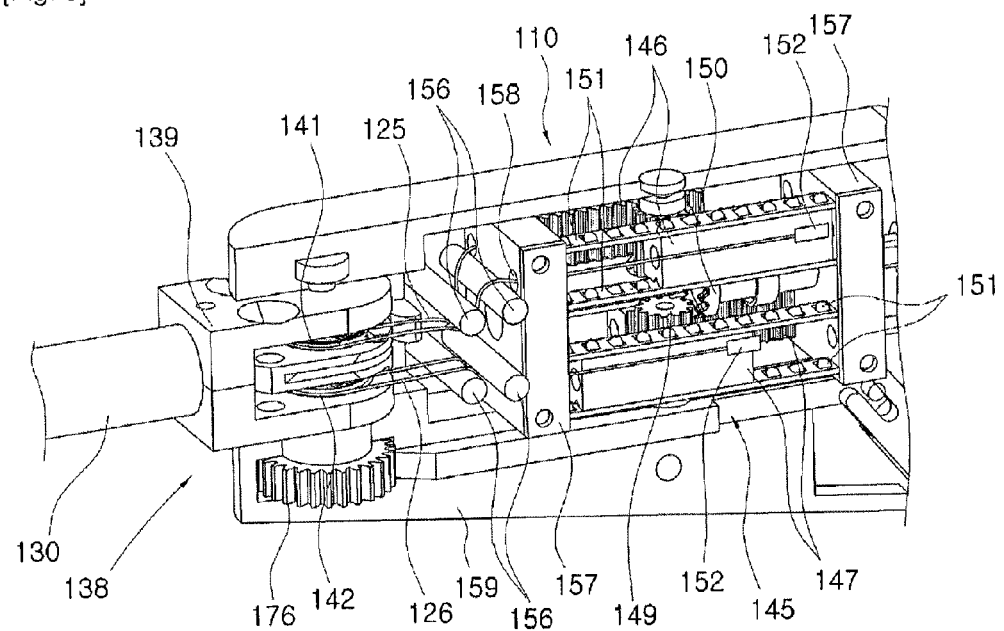

[Fig. 9]
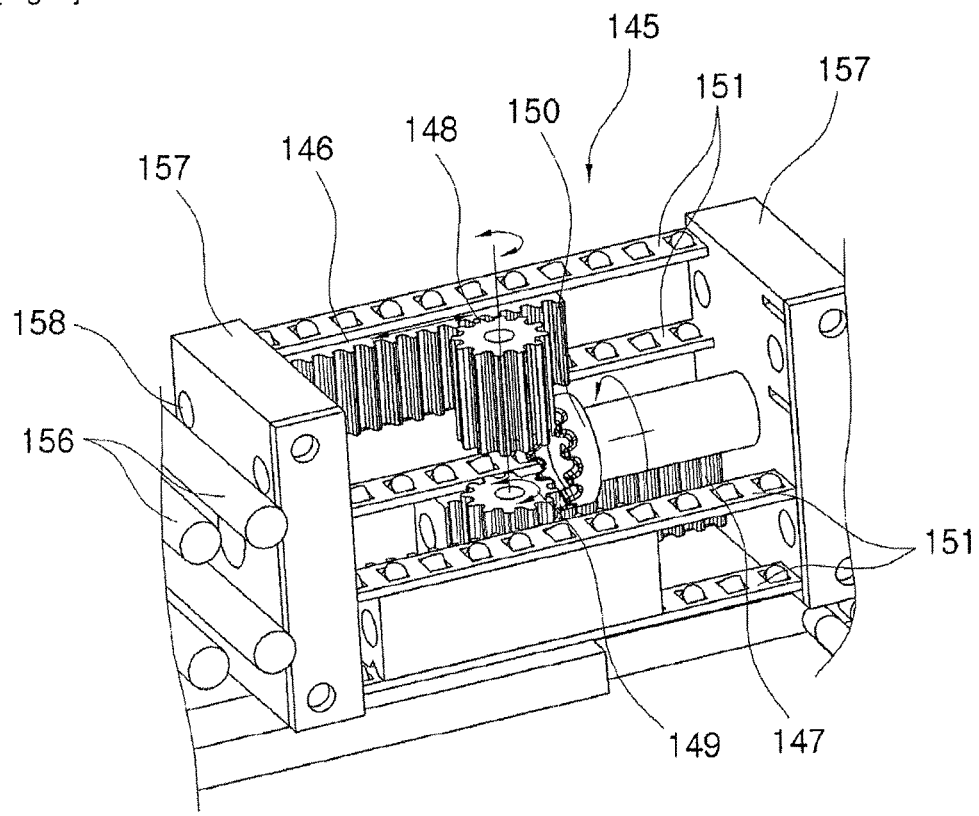
[Fig. 10]
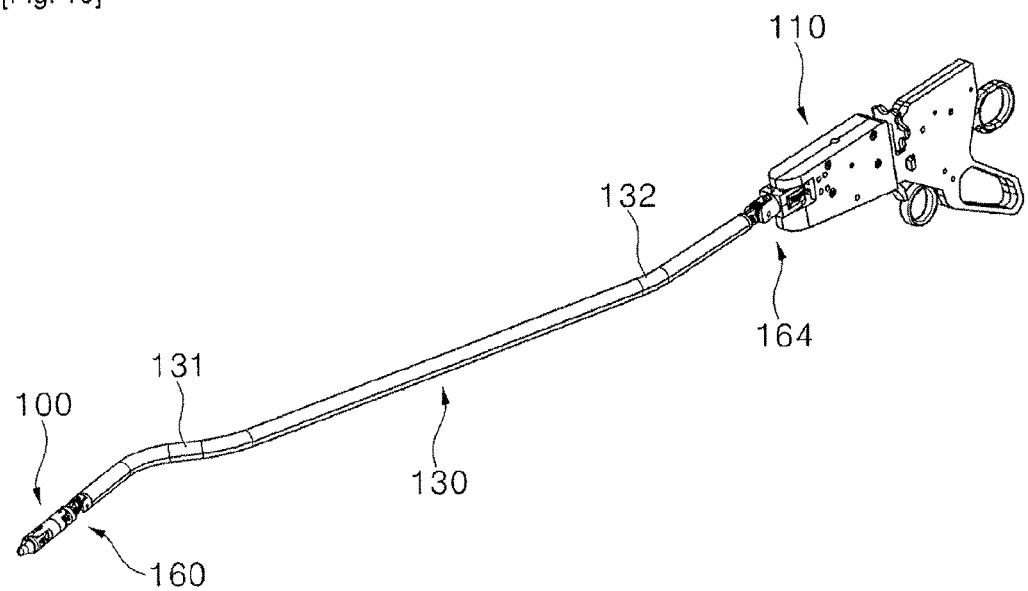

[Fig. 11]
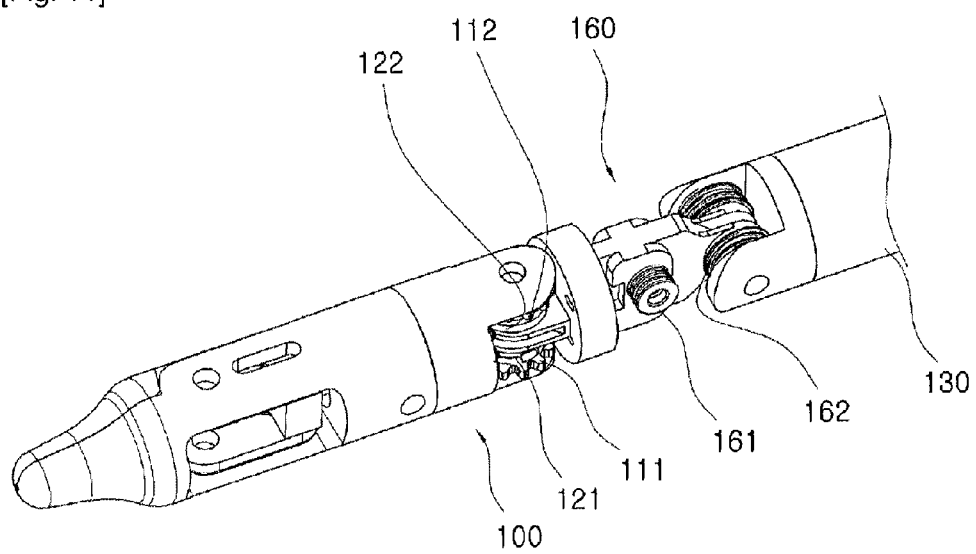
[Fig. 12]
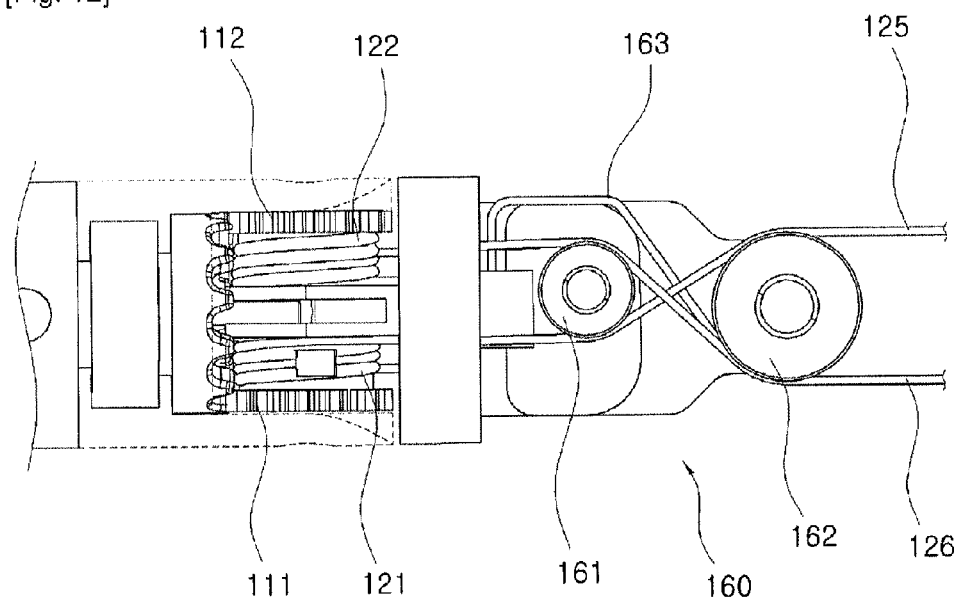

[Fig. 13]
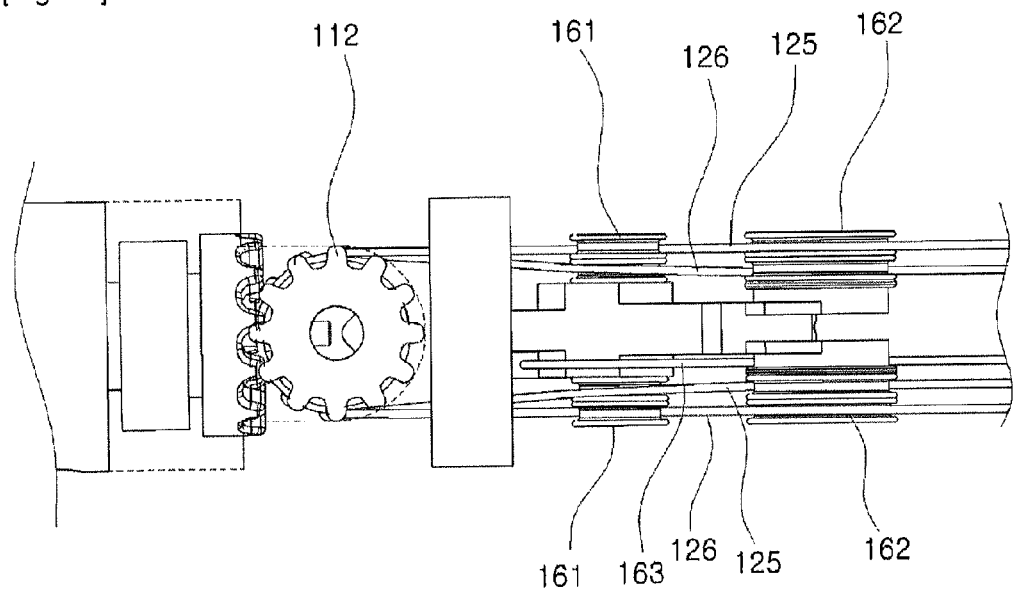
[Fig. 14]
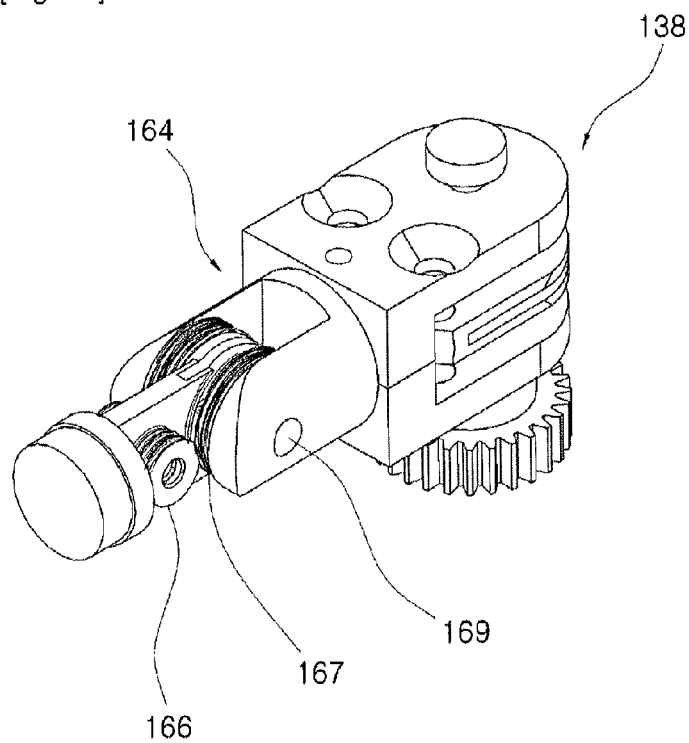

[Fig. 15]
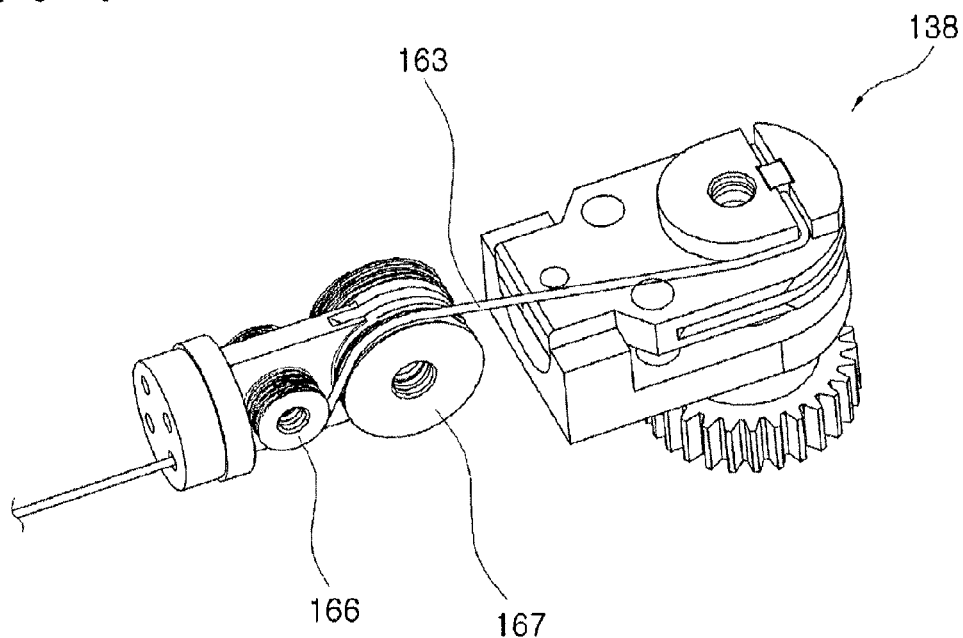
[Fig. 16]
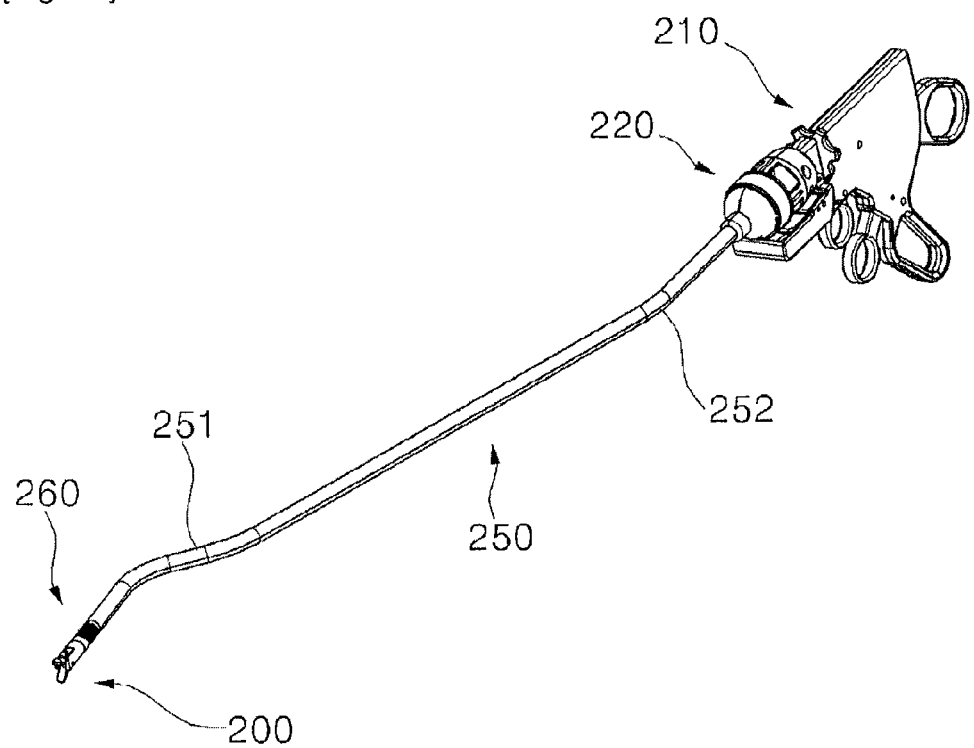

[Fig. 17]
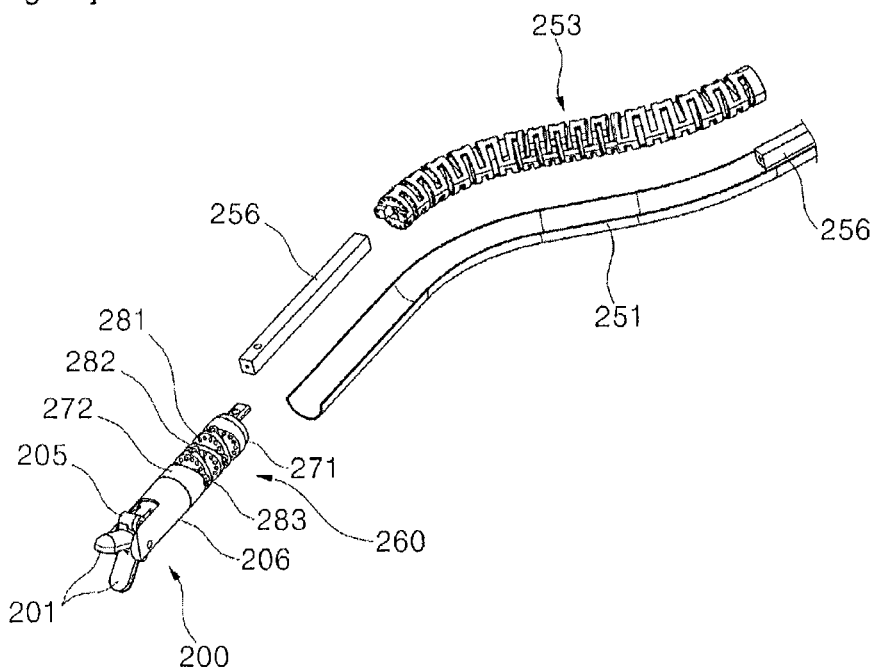
[Fig. 18]
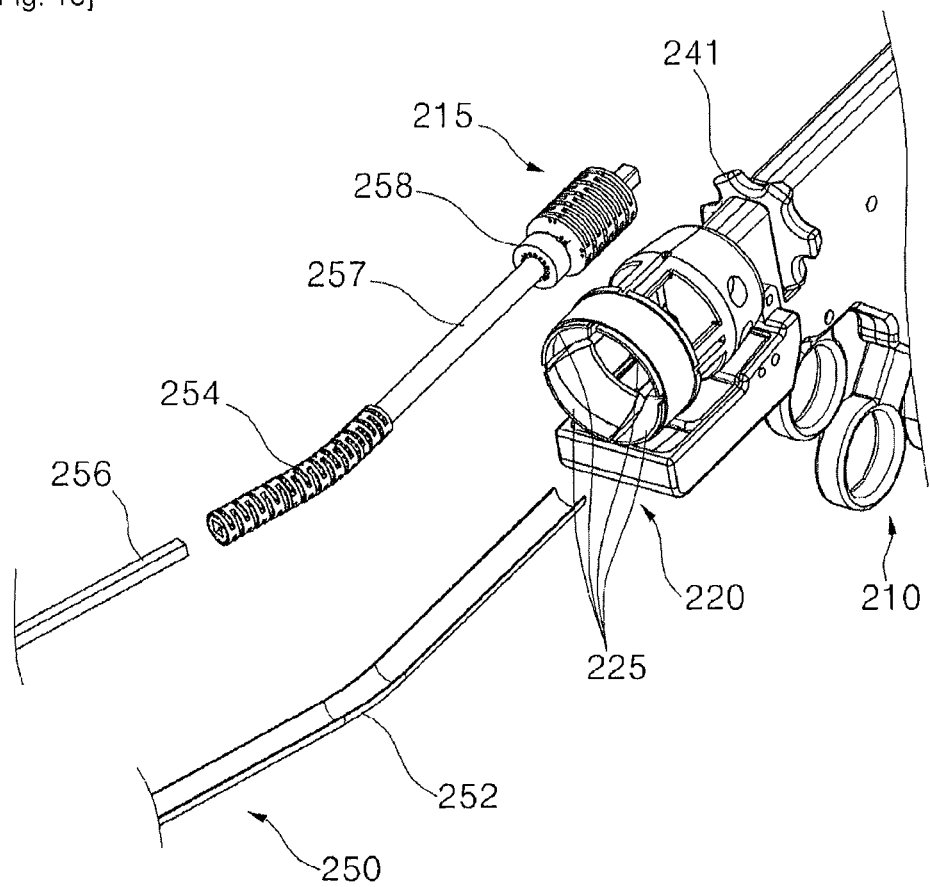

[Fig. 19]
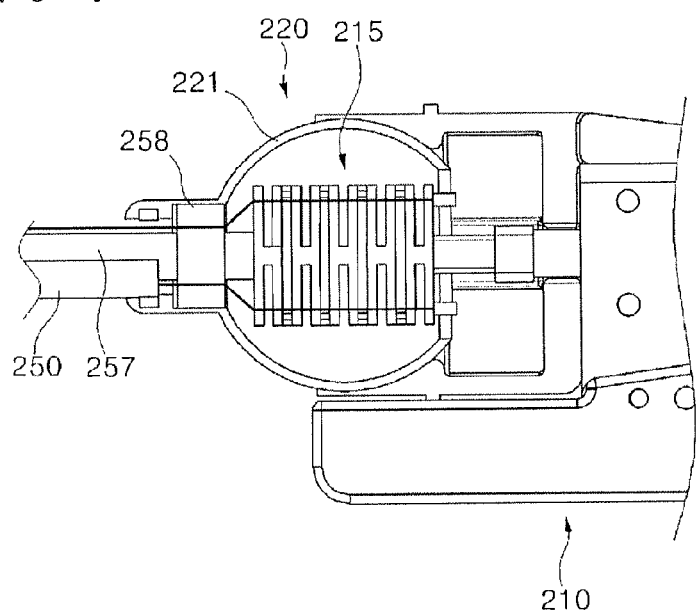
[Fig. 20]
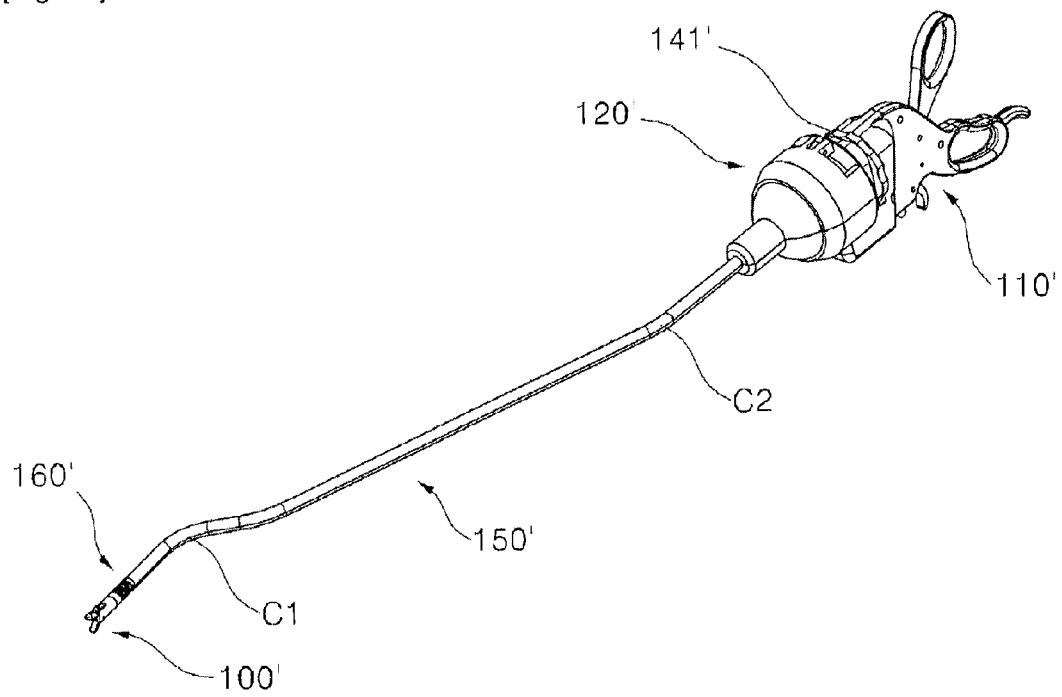

[Fig. 21]
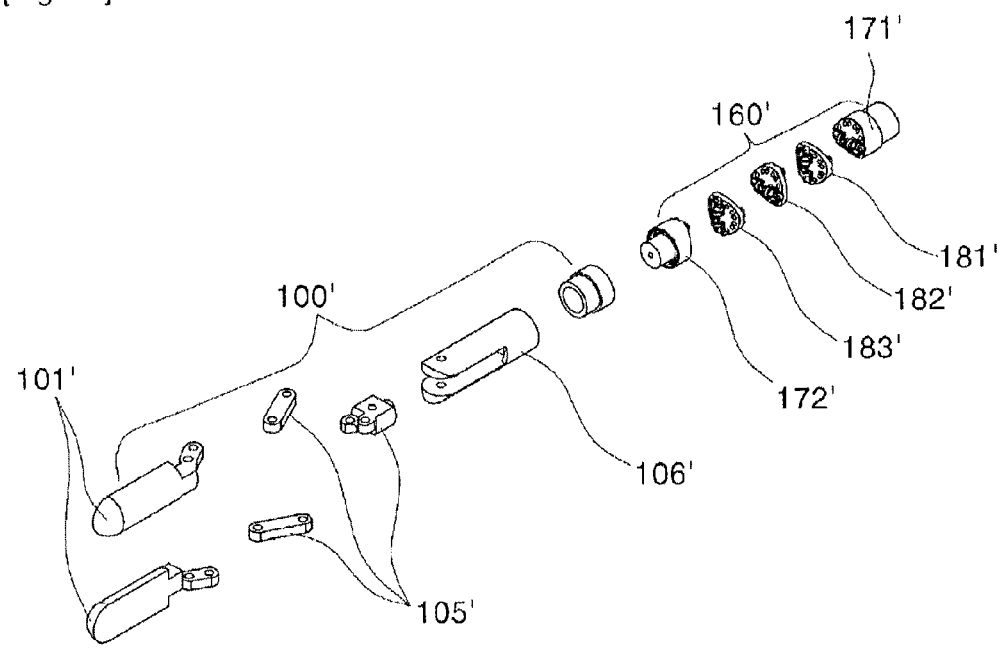
[Fig. 22]
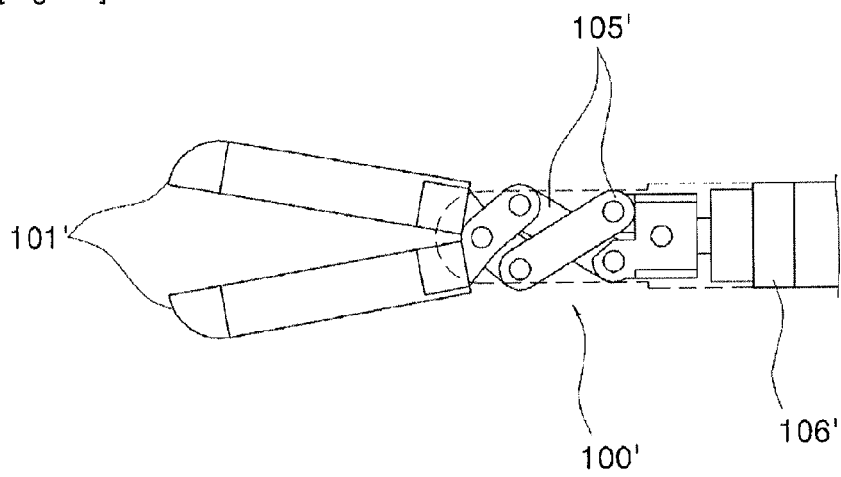

[Fig. 23]
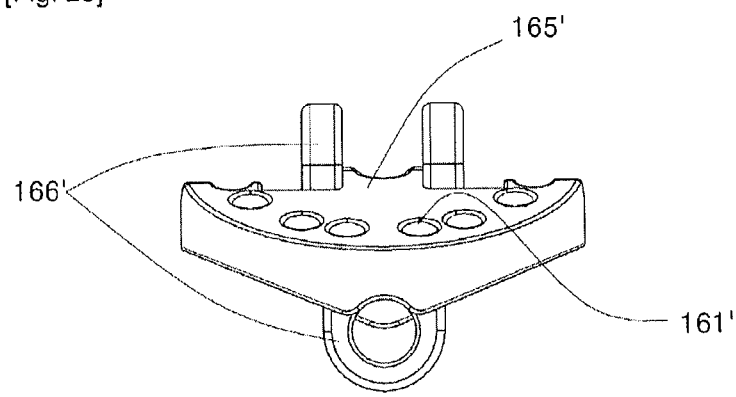
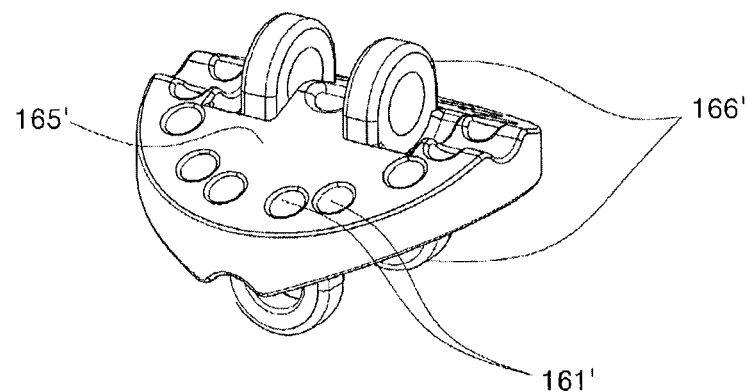
[Fig. 24]
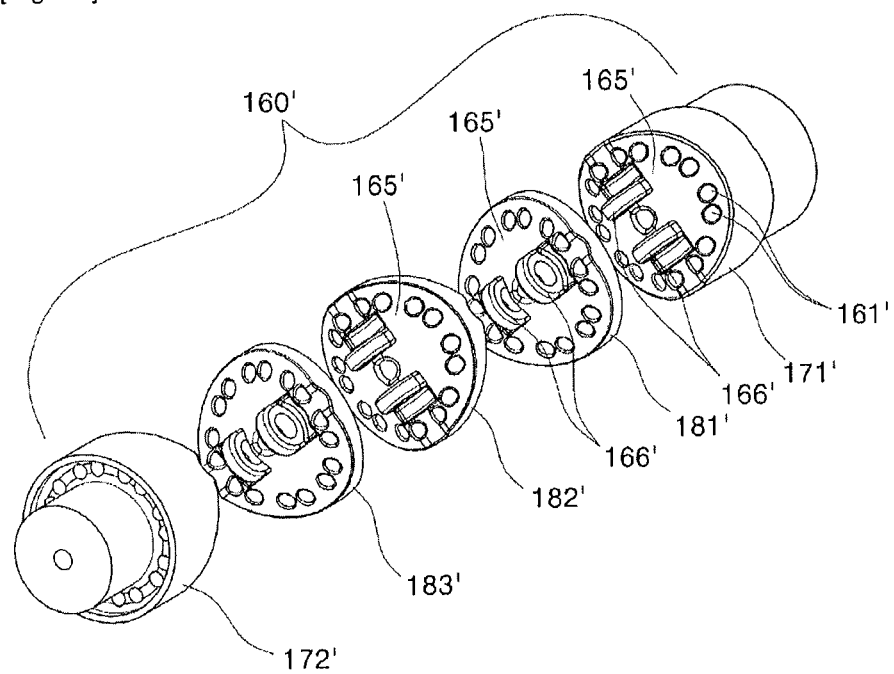

[Fig. 25]
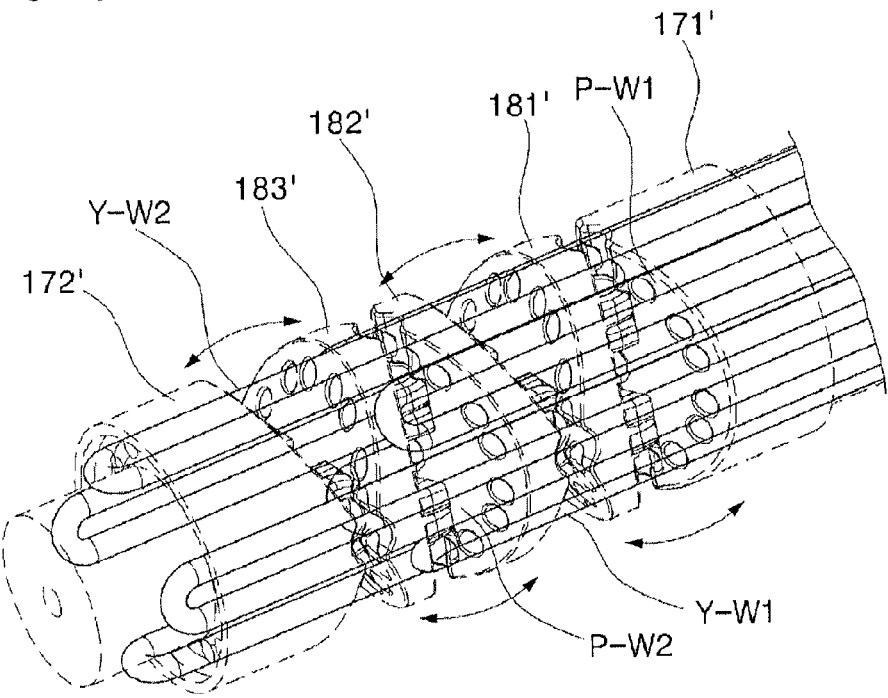
[Fig. 26]
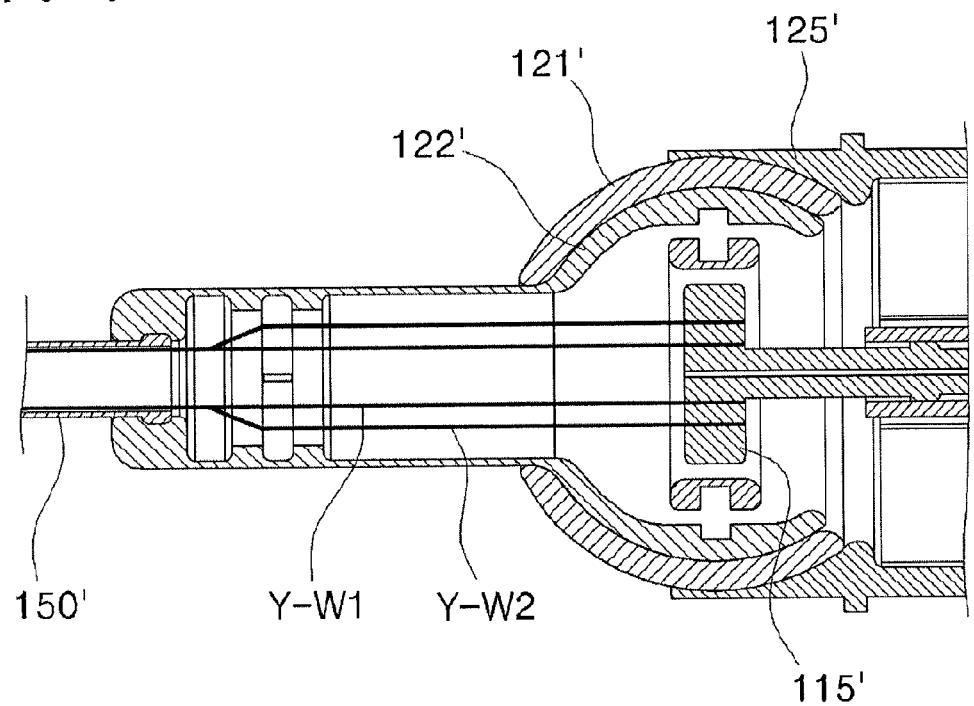

[Fig. 27]
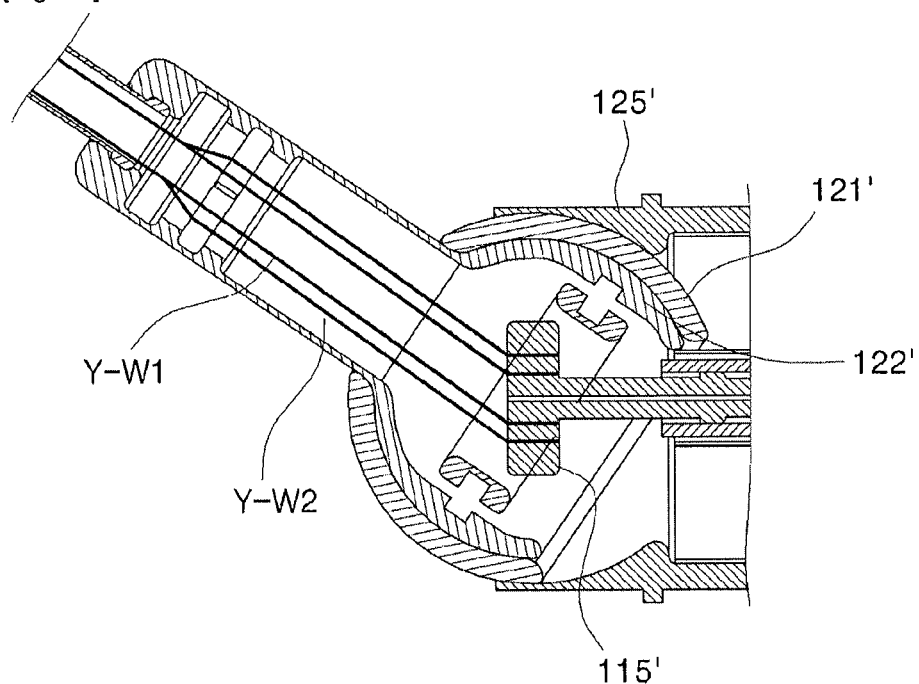
[Fig. 28]
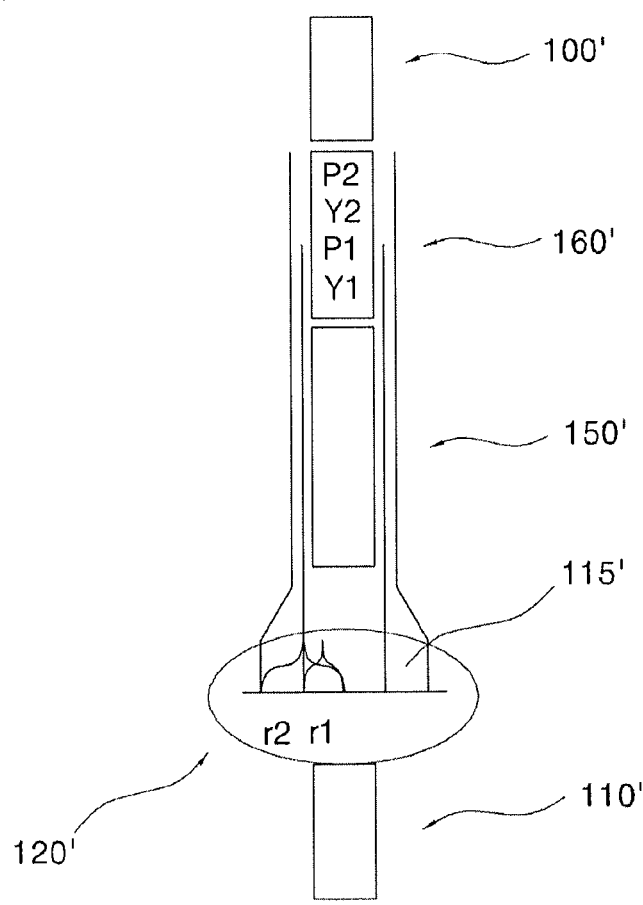

[Fig. 29]
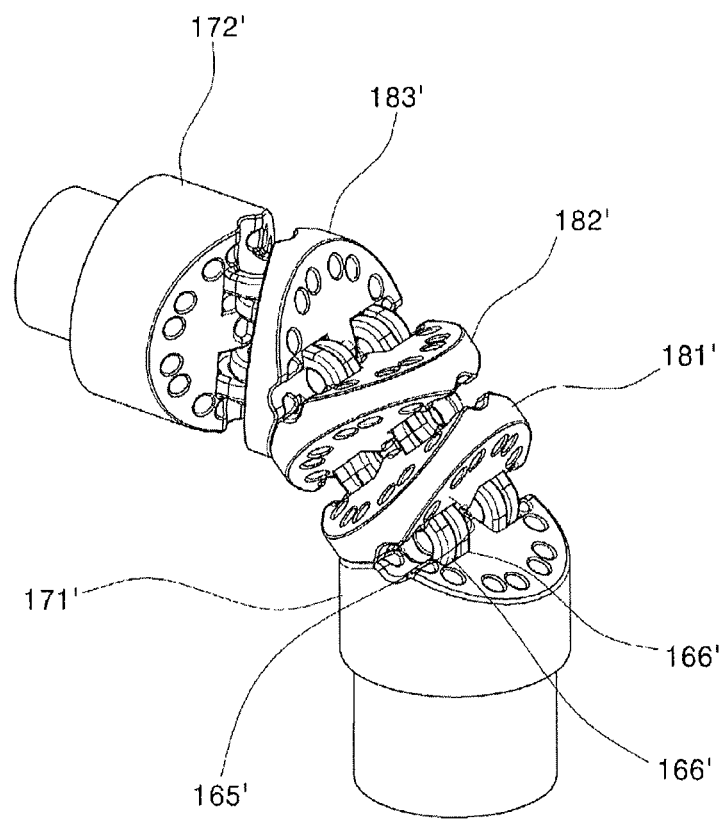
[Fig. 30]
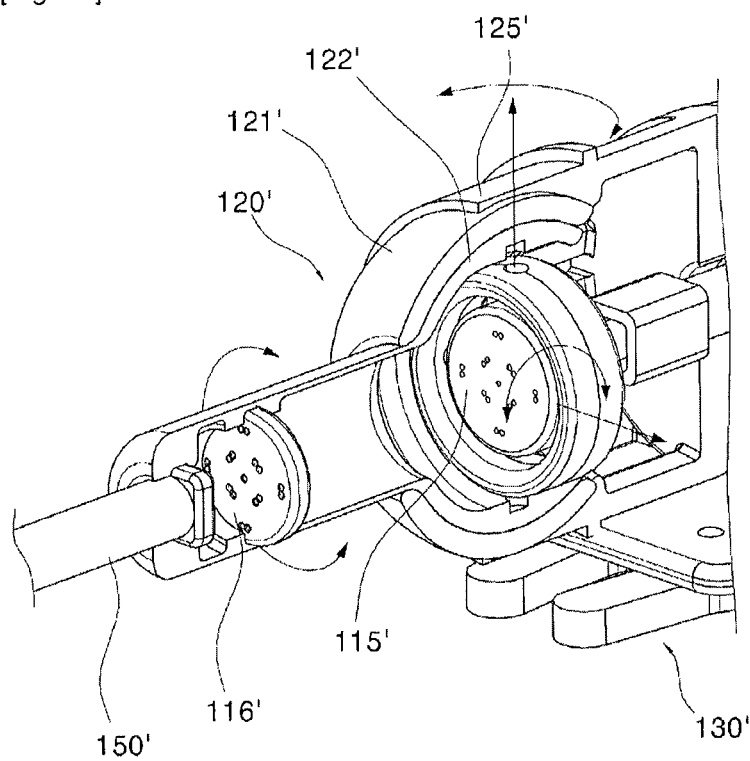

[Fig. 31]
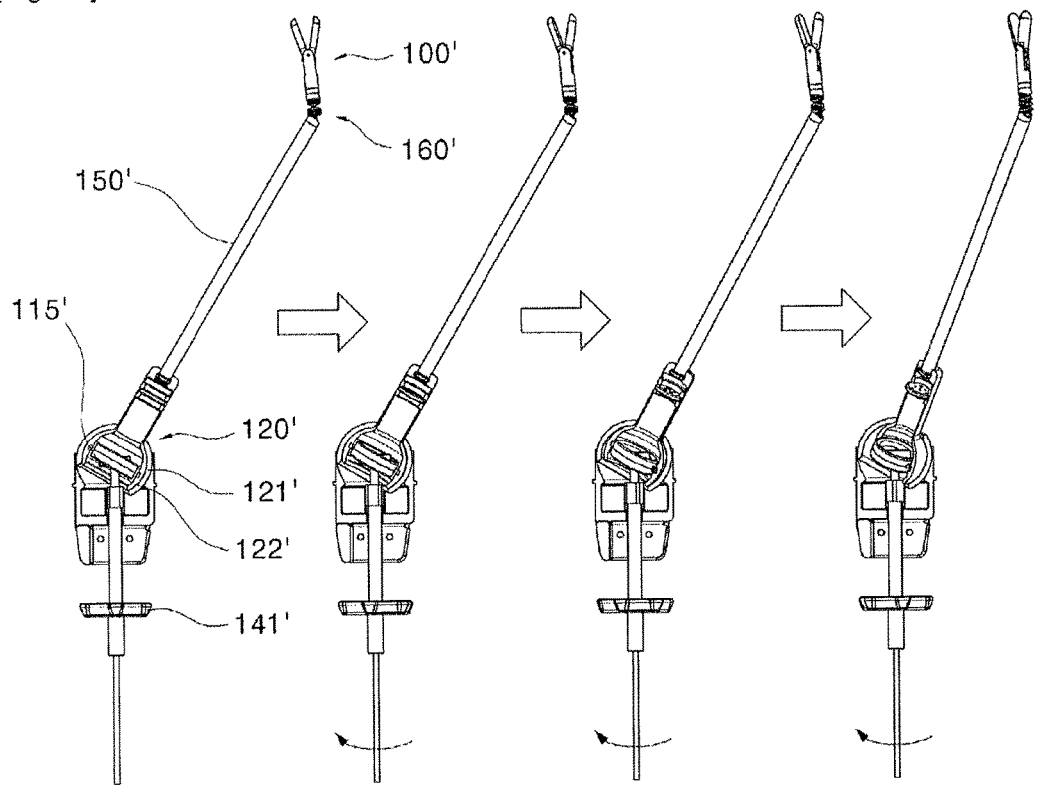
[Fig. 32]
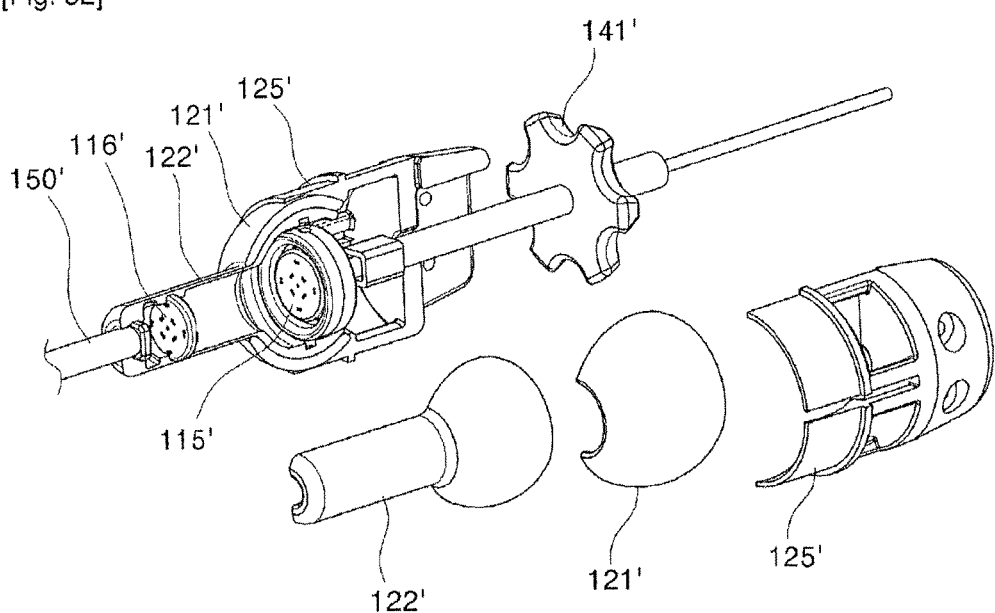

[Fig. 33]
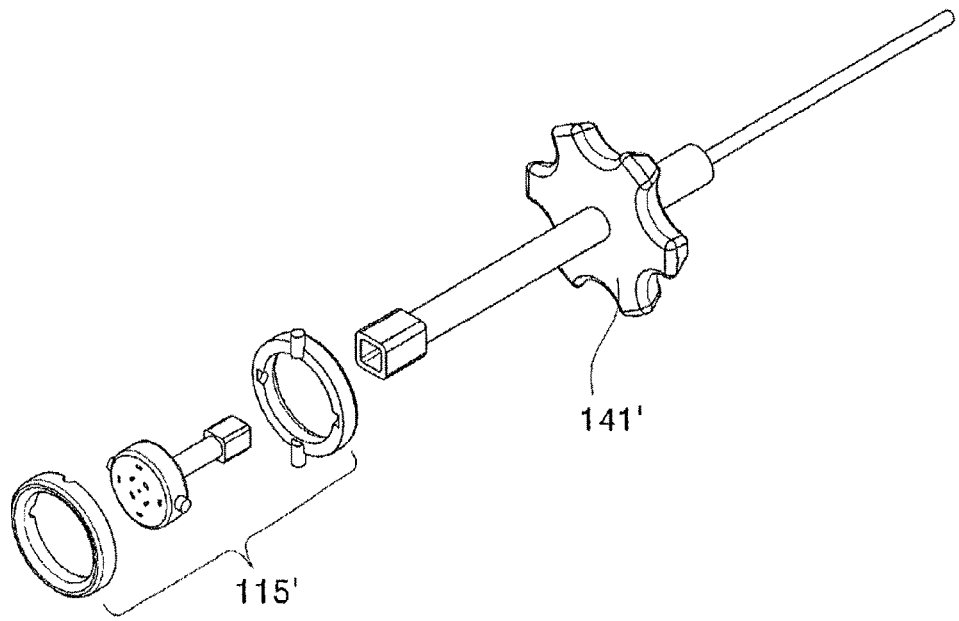
[Fig. 34]
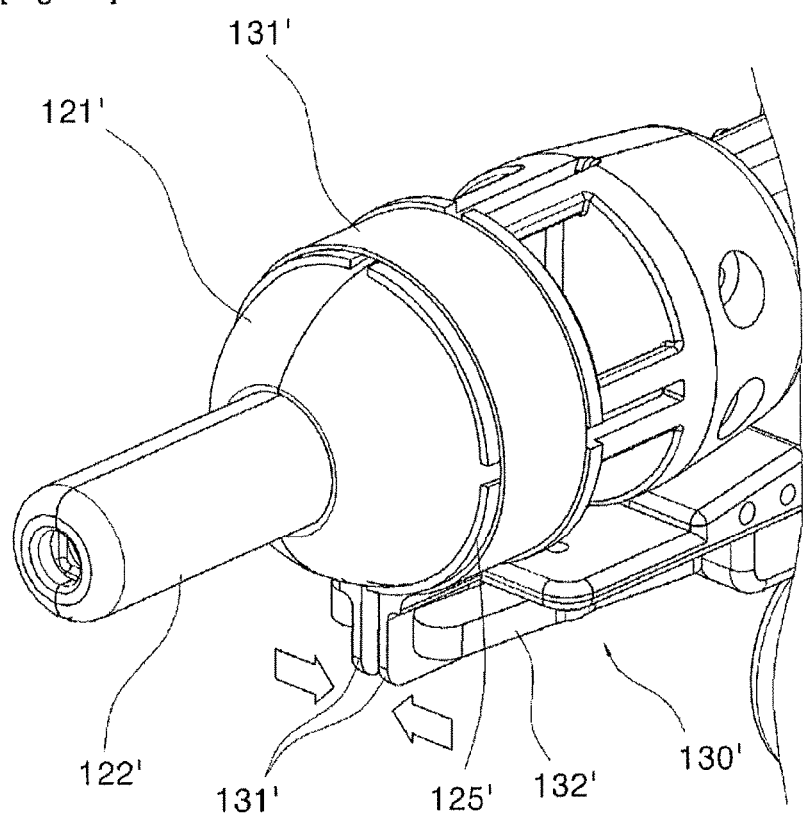

[Fig. 35]
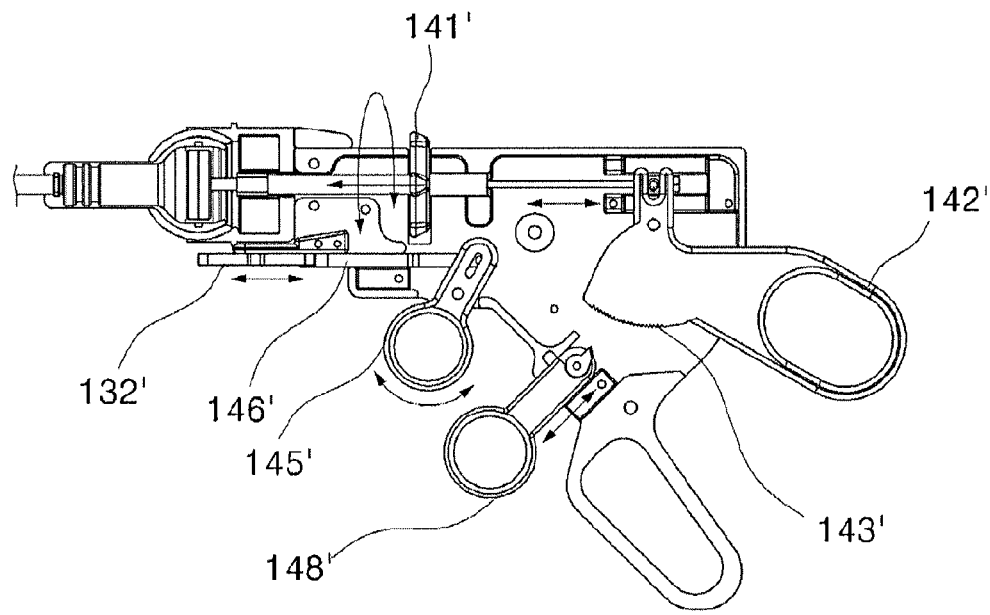
[Fig. 36]
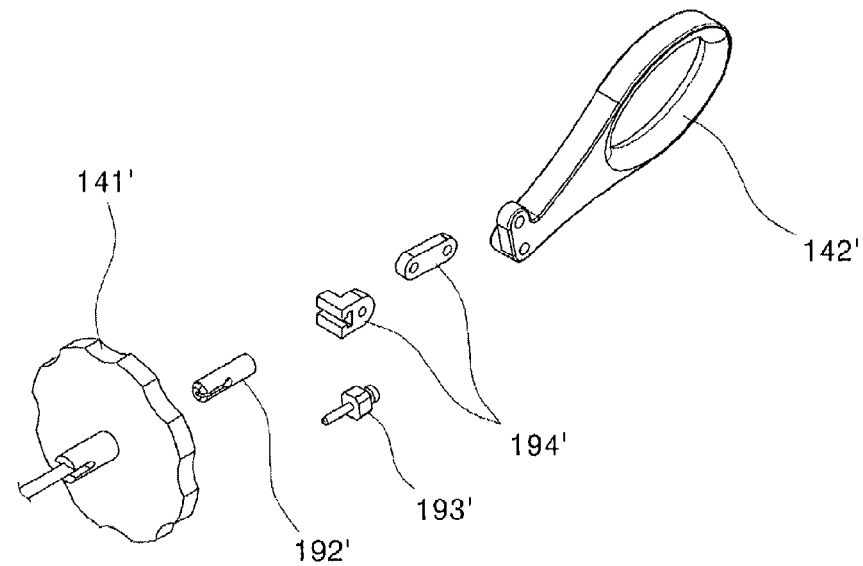
[Fig. 37]
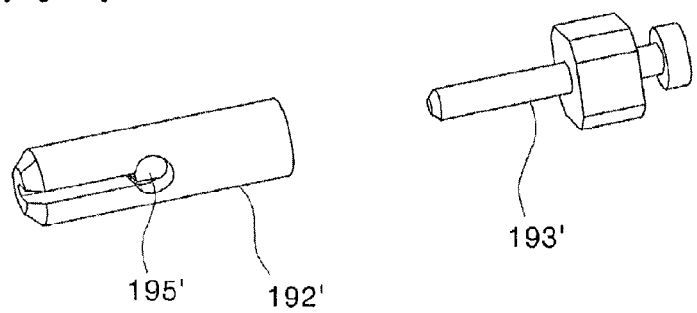

[Fig. 38]
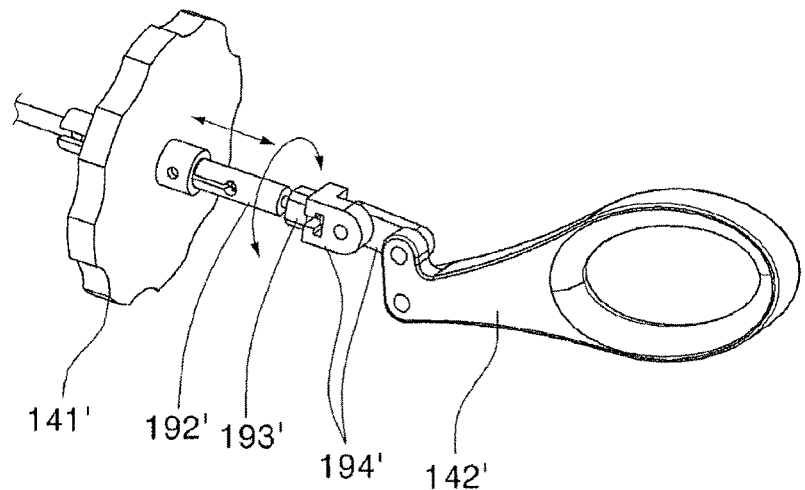
[Fig. 39]
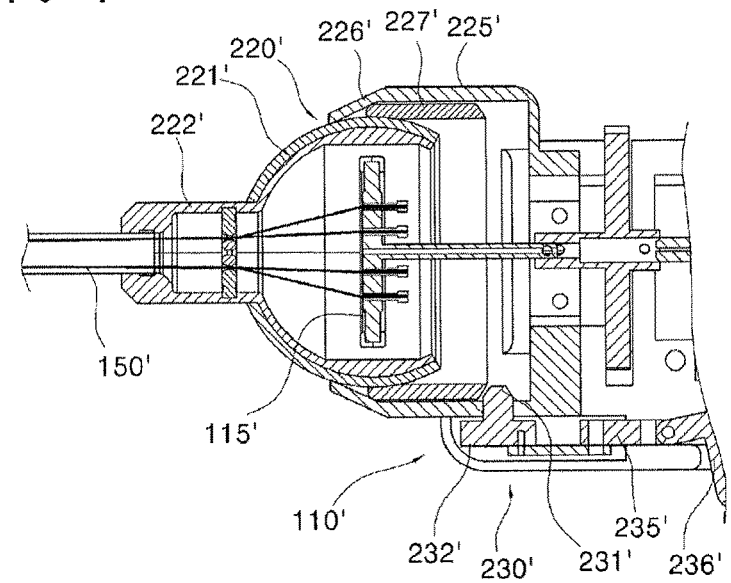
[Fig. 40]
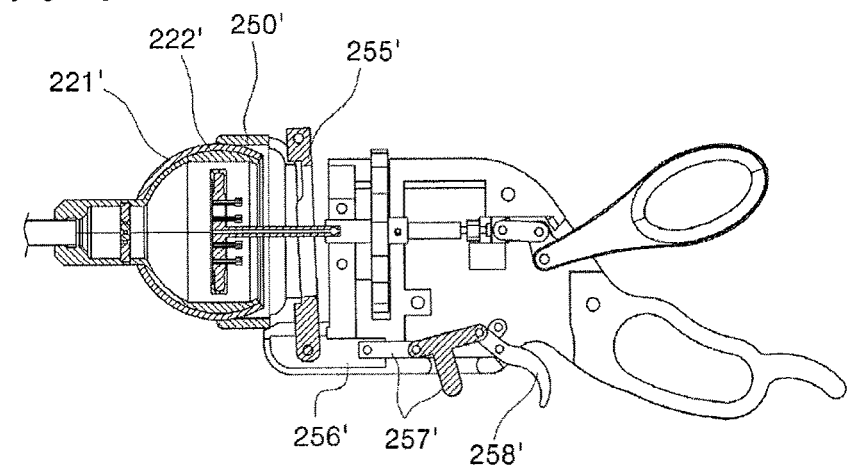

[Fig. 41]
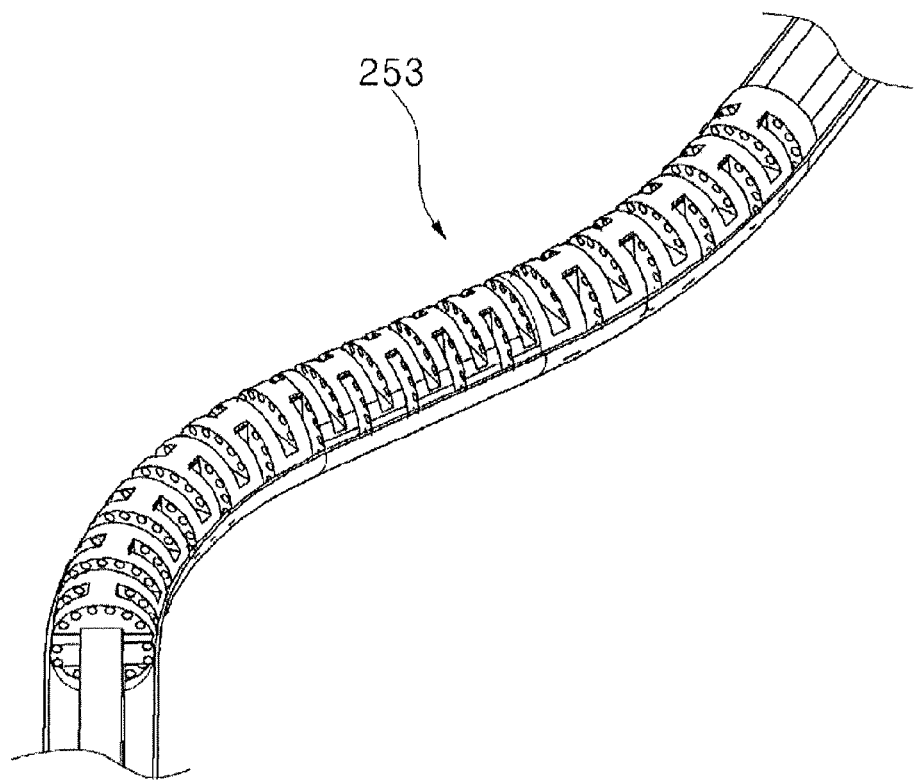
[Fig. 42]
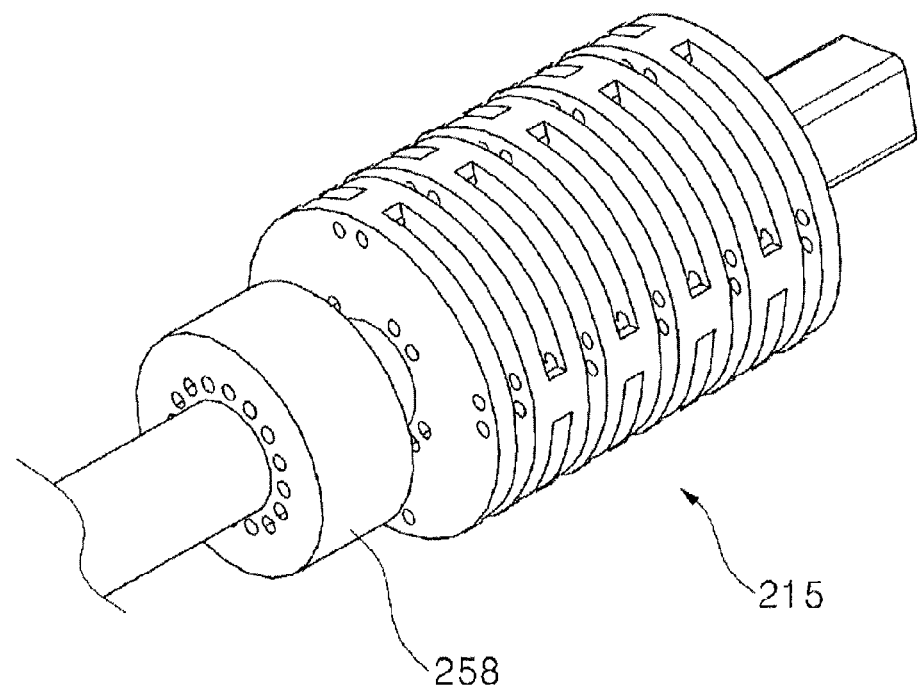

[Fig. 43]
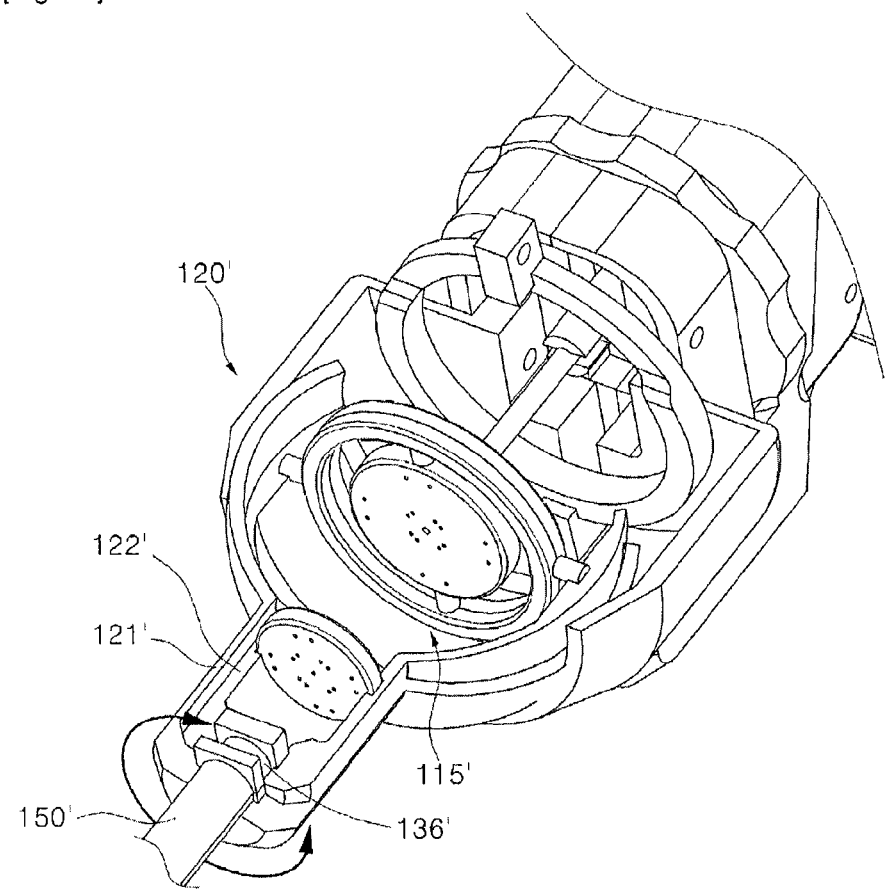
[Fig. 44]
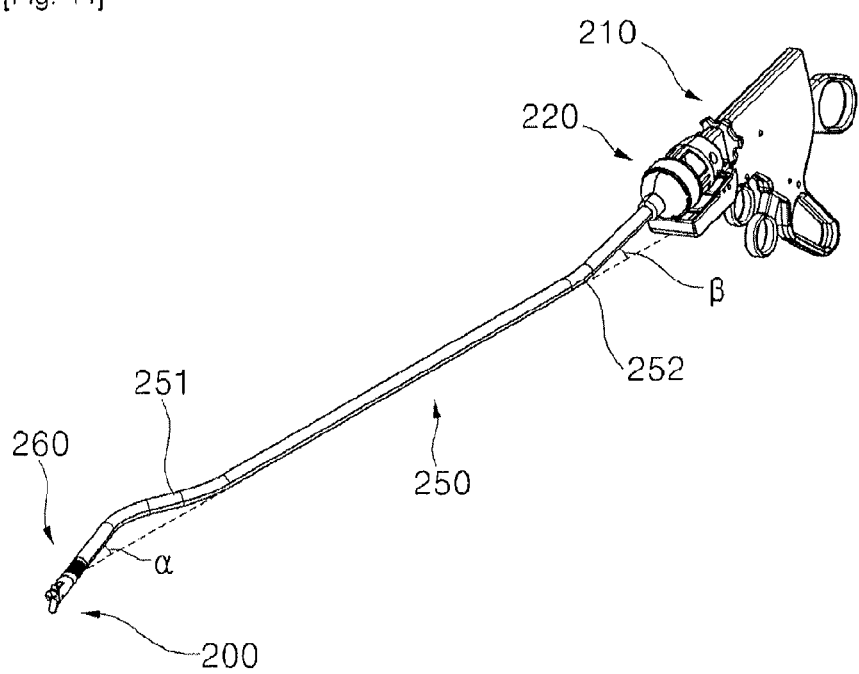

MINIMALLY INVASIVE SURGICAL INSTRUMENT HAVING A BENT SHAFT

FIELD OF THE INVENTION

The present invention relates to a minimally invasive surgical instrument having a bent shaft, and more particularly to a minimally invasive surgical instrument in which at least a part of a shaft includes a bend.

BACKGROUND

Minimally invasive surgery is a surgical approach that involves the use of instruments inserted through several tiny incision openings to perform a surgery causing minimal tissue trauma in human or animal bodies.

The minimally invasive surgery relatively reduces changes in metabolism of a patient in the period of post-surgical care, so it facilitates rapid recovery of the patient. Therefore, the minimally invasive surgery shortens the length of hospitalization of the patient after the surgery and allows the patient to return to normal physical activities in a short period of time. In addition, the minimally invasive surgery causes less pain and leaves fewer scars on the patient's body after the surgery.

One of the general forms of the minimally invasive surgery is endoscopy. Among the others, a laparoscopy that involves minimally invasive inspection and operation inside abdominal cavity is known as the most general form of endoscopy. To operate a standard laparoscopic surgery, the abdomen of the patient is insufflated with gas and at least one small incision is formed to provide an entrance for laparoscopic surgical instruments, through which a trocar is inserted. When performing the surgery, it is general that a user puts the laparoscopic surgical instruments into a surgical site or the like through the trocar, and manipulates (or controls) the instruments from the outside of abdominal cavity. In general, the laparoscopic surgical instruments include a laparoscope (for observation of a surgical site) and other working tools. Herein, the working tools are similar to the conventional tools used for small incision surgery, except that the end effector or working end of each tool is separated from its handle or the like by a shaft. For instance, the working tools may include a clamp, a grasper, scissors, a stapler, a needle holder, and so forth. Meanwhile, the user monitors the procedure of the surgery through a monitor that displays the images of the surgical site which are taken by the laparoscope. The endoscopic approaches similar to the above are broadly used in retroperitoneoscopy, pelviscopy, arthroscopy, cisternoscopy, sinuscopy, hysteroscopy, nephroscopy, cystoscopy, urethroscopy, pyeloscopy, and so on.

The inventor(s) has developed various minimally invasive surgical instruments useful for the above-mentioned minimally invasive surgeries and has already disclosed the features of the structures and effects of the same in Korean Patent Application Nos. 2008-51248, 2008-61894, 2008-79126 and 2008-90560, the contents of which are incorporated herein by reference in its entirety. Additionally, the inventor(s) have also introduced a minimally invasive surgical instrument with improved functionality, which is more advantageous for users and patients, in Korean Patent Application Nos. 2010-115152 and 2011-3192, the contents of which are incorporated herein by reference in its entirety.

Herein, the inventor(s) now present a minimally invasive surgical instrument that may be more conveniently manipulated by a user while retaining the functional advantages of the minimally invasive surgical instruments disclosed in the above Korean applications.

SUMMARY OF THE INVENTION

One object of the present invention is to solve all the above problems in prior art.

Another object of this invention is to provide a minimally invasive surgical instrument having a bent shaft wherein an end effector has good characteristics in terms of its roll direction operation.

Yet another object of this invention is to provide a minimally invasive surgical instrument wherein the collision of end effectors may be avoided when two or more minimally invasive surgical instruments are used together.

Still another object of this invention is to provide a minimally invasive surgical instrument wherein the interference of handling units may be avoided when two or more minimally invasive surgical instruments are used together.

According to one aspect of the invention to achieve the objects as described above, there is provided a minimally invasive surgical instrument comprising: a shaft; an end effector connected to one end of the shaft; a joint unit interposed between the shaft and the end effector; and a plurality of wires connected to the joint unit to enable the end effector to carry out joint motion, wherein the shaft comprises at least one bend, and the at least one bend may transmit therein force to operate the end effector in a roll direction, independently of the shaft.

In addition, there may be provided other ways to implement this invention.

According to the invention, there is provided a minimally invasive surgical instrument having a bent shaft wherein an end effector has good characteristics in terms of its roll direction operation.

According to the invention, there is provided a minimally invasive surgical instrument wherein the collision of end effectors may be avoided when two or more minimally invasive surgical instruments are used together.

According to the invention, there is provided a minimally invasive surgical instrument wherein the interference of handling units may be avoided when two or more minimally invasive surgical instruments are used together.

BRIEF DESCRIPTION OF THE DRAWINGS

FIG. 1 shows the overall appearance of a minimally invasive surgical instrument according to one embodiment of the invention.

FIG. 2 shows the interior of a first bend 131 and a second bend 132 of FIG. 1.

FIG. 3 is a cross-sectional view of a first flexible resin 133 of FIG. 2.

FIG. 4 shows the configuration of the first flexible resin 133 of FIG. 2 in detail.

FIG. 5 is an exploded view of a part of a handling unit 110 of FIG. 1.

FIG. 6 shows the overall appearance of a minimally invasive surgical instrument according to another embodiment of the invention.

FIG. 7 is an enlarged view of an end effector 100 shown in FIG. 6.

FIG. 8 is an enlarged view of a handling unit 110 shown in FIG. 6.

FIG. 9 is an enlarged view of a roll control unit 145 shown in FIG. 8.

FIG. 10 shows the overall appearance of a minimally invasive surgical instrument according to yet another embodiment of the invention.

FIG. 11 shows an enlarged view of an end effector 100 and a pitch operating unit 160 shown in FIG. 10.

FIG. 12 shows a lateral view of the pitch operating unit 160 shown in FIG. 11, and FIG. 13 shows a top view of the same.

FIG. 14 shows a perspective view of a pitch control unit 164 and a yaw control unit 138 shown in FIG. 10, and FIG. 15 shows an exploded perspective view of some components of the same.

FIG. 16 shows the overall appearance of a minimally invasive surgical instrument according to still another embodiment of the invention.

FIG. 17 is an exploded view of a first bend 251 of FIG. 16.

FIG. 18 is an exploded view of a second bend 252 and a rotation manipulation unit 220 of FIG. 16.

FIG. 19 is a lateral view of the rotation manipulation unit 220 of FIG. 16.

FIG. 20 shows the overall appearance of a minimally invasive surgical instrument according to still yet another embodiment of the invention.

FIG. 21 is an exploded view of some components of FIG. 20.

FIG. 22 is a lateral view of an end effector 100' according to one embodiment of the invention.

FIG. 23 shows lateral and perspective views of a joint link according to one embodiment of the invention.

FIG. 24 is an exploded view of a joint unit 160' according to one embodiment of the invention.

FIG. 25 shows a plurality of wires P-W1, Y-W1, P-W2 and Y-W2 arranged in the joint unit 160' shown in FIG. 24.

FIGS. 26 and 27 show the interior of a rotation manipulation unit 120' according to one embodiment of the invention.

FIG. 28 shows how joint motion is carried out in the joint unit 160' by a gyro link 115' of the rotation manipulation unit 120' according to one embodiment of the invention.

FIG. 29 shows the joint unit 160' in which the joint motion has been carried out according to one embodiment of the invention.

FIG. 30 is a detailed diagram of the rotation manipulation unit 120' according to one embodiment of the invention.

FIG. 31 shows a sequence of the rolling operation of the end effector 100' according to one embodiment of the invention.

FIG. 32 is an exploded view of the rotation manipulation unit 120' according to one embodiment of the invention.

FIG. 33 is an exploded view of the gyro link 115' according to one embodiment of the invention.

FIG. 34 shows a specific example of a configuration to fix a handling unit 110' to an external rotating drum 121' according to one embodiment of the invention.

FIG. 35 shows the interior of the handling unit 110' according to one embodiment of the invention.

FIG. 36 is an exploded view showing the connection between a roll sprocket 141' and an opening/closing handle 142' according to one embodiment of the invention.

FIGS. 37 and 38 are enlarged perspective views of the above connection.

FIG. 39 shows the interior of a rotation manipulation unit 220' according to another embodiment of the invention.

FIG. 40 is a diagram of a rotation manipulation unit 220' according to yet another embodiment of the invention.

FIG. 41 is an enlarged view of a first flexible resin 253 of FIG. 17.

FIG. 42 is a detailed diagram of a flexible link 215 and an annular member 258 of FIG. 18.

FIG. 43 shows the interior of a rotation manipulation unit 120' of a minimally invasive surgical instrument according to still another embodiment of the invention.

FIG. 44 shows the respective angles from the body of a shaft 250 to one end of the first bend 251 facing an end effector 200 and to the second bend 252 in FIG. 16.

DETAILED DESCRIPTION OF THE PREFERRED EMBODIMENTS

In the following detailed description of the invention, references are made to the accompanying drawings that show, by way of illustration, specific embodiments in which the invention may be practiced. These embodiments are described in sufficient detail to enable those skilled in the art to practice the invention. It is to be understood that the various embodiments of the invention, although different from each other, are not necessarily mutually exclusive. For example, specific shapes, structures, or characteristics described herein may be implemented as modified from one embodiment to another embodiment without departing from the spirit and the scope of the invention. Furthermore, it shall be understood that the locations or arrangements of individual elements within each embodiment may be also modified without departing from the spirit and the scope of the invention. Therefore, the following detailed description is not to be taken in a limiting sense, and the scope of the invention is to be taken as encompassing the scope of the appended claims and all equivalents thereof. In the drawings, like reference numerals refer to the same or similar elements throughout the several views.

Hereinafter, preferred embodiments of the present invention will be described in detail with reference to the accompanying drawings to enable those skilled in the art to easily implement the invention.

First Embodiment

FIG. 1 shows the overall appearance of a minimally invasive surgical instrument according to one embodiment of the invention. Further, FIG. 2 shows the interior of a first bend 131 and a second bend 132 of FIG. 1

Reference will be made to FIG. 1. The minimally invasive surgical instrument according to the present embodiment may comprise an end effector 100 to perform surgery by using surgical tools (not shown) or functioning itself as a surgical tool; a handling unit 110 to control the operation of the end effector 110 according to a user's manipulation; a shaft 130 to connect the end effector 100 and the handling unit 110, wherein the end effector 100 is disposed at one end of the shaft 130 such that it may operate in a roll direction and the handling unit 110 is disposed at the other end; and a first bend 131 and a second bend 132 in the shaft 130. As shown, the first bend 131 may be disposed close to the end effector 100, and the second bend 132 may be disposed close to the handling unit 110. The first bend 131 may be formed in a curved shape as shown so that the collision or the like of the end effectors 100 may be avoided when two or more minimally invasive surgical instruments are used together. The second bend 232 may be formed in a shape spreading from the longitudinal central axis of the shaft 130 to the outside as shown, so that the interference or the like of the handling units 110 may be avoided when two or more minimally invasive surgical instruments are used together.

Reference will be made to FIG. 2. The shaft 130 may include therein a first flexible resin 133, a second flexible resin 134 and a plurality of linear members 136 (the flexible resin may be formed from Teflon or the like, and the preferably cylindrical linear members 136 may be formed from a rigid material). The first flexible resin 133 and the second flexible resin 134 may substantially correspond to the first bend 131 and the second bend 132 of the shaft 130 located outside the flexible resins, respectively, so that they are connected between the end effector 100 and the handling unit 110 by means of the linear members 136. When the user rotates a roll sprocket 155 included in the handling unit 110, the flexible resins 133 and 134 may operate the end effector 100 in the roll direction even though the shaft 130 does not operate in the roll direction (in this case, the flexible resins 133 and 134 and the linear members 136 may also operate in the roll direction together with the end effector 100).

FIG. 3 is a cross-sectional view of the first flexible resin 133 of FIG. 2. Further, FIG. 4 shows the configuration of the first flexible resin 133 of FIG. 2 in detail.

Reference will be made to FIGS. 3 and 4. As shown in FIG. 4, the first flexible resin 133 may have a configuration in which a bending member A bendable in a pitch direction and a bending member B bendable in a yaw direction are alternately arranged. The bending member A may be comprised of two annular members (a1 and a3) and one connecting member (a2) to connect the annular members therebetween (the connecting member a2 may preferably be disposed on a central axis of the annular members a1 and a3). The connecting member a2 may allow the bending member A to bend only in the pitch direction. In the same way, the bending member B may be configured to bend only in the yaw direction.

FIG. 5 is an exploded view of a part of the handling unit 110 of FIG. 1.

Reference will be made to FIG. 5. The linear members 136 are connected with the roll sprocket 155 so that when the user rotates the roll sprocket 155, the rotation may be transmitted to the second flexible resin 134, the first flexible resin 133 and the end effector 100 connected thereto. In this case, the shaft 130 does not operate in the roll direction while only the flexible resins 133 and 134 and the linear members 136 operate in the roll direction. Eventually, the end effector 100 may operate in the roll direction almost without any other operations. Meanwhile, when the user manipulates a rotatable handle 113 of the handling unit 110, the opening/closing wires 179 connected thereto are pushed or pulled to open or close the end effector 100, as disclosed in the above-mentioned Korean applications.

With regard to the various following embodiments, the configurations which are different or modified from that of the first embodiment will be mainly described below.

Second Embodiment

FIG. 6 shows the overall appearance of a minimally invasive surgical instrument according to another embodiment of the invention.

Reference will be made to FIG. 6. The minimally invasive surgical instrument according to the present embodiment may comprise an end effector 100, a handling unit 110, a shaft 130, a first bend 131 and a second bend 132, in the same manner as the first embodiment. According to the present embodiment, the end effector 100 may carry out not only the roll direction and/or opening/closing operations but also the yaw direction operation.

The minimally invasive surgical instrument according to the present embodiment is basically configured based on the principles disclosed in the above-mentioned Korean Patent Application No. 2010-115152, while its shaft 130 may include the first bend 131 and the second bend 132 in the same manner as the first embodiment. However, the first bend 131 or the second bend 132 herein does not necessarily need to include the flexible resin.

There follows the description of FIGS. 2 to 4 (herein, FIGS. 7 to 9) related to the first embodiment disclosed in Korean Application No. 2010-115152, which corresponds to the present embodiment.

FIG. 7 is an enlarged view of the end effector 100 shown in FIG. 6.

As illustrated, the end effector 100 may comprise pincers 101 (also referred to as "holders") to hold surgical instruments. The pincers 101 can be opened or closed by an opening/closing wire (not shown). The opening/closing wire may transmit the force for opening or closing the pincers 101 from the handling unit 110 to the pincers 101 since one end of the wire is connected to the pincers 101 and the other end is connected to the handling unit 110. An elastic component such as a spring (not shown) may be used together to control either of the opening or closing of the pincers 101.

Meanwhile, the end effector 100 may comprise a connecting component 105 for connecting and fixing the pincers 101 or the like to a roll gear 106 (to be described below) to enable the pincers 101 or the like to operate in the roll direction; the roll gear 106 to operate the pincers 101 or the like and the connecting component 105 in the roll direction; and a first pinion 111 and a second pinion 112 geared to the roll gear 106 on the opposite side of the connecting component 105 to rotate the roll gear 106. A first pulley 121 and a second pulley 122 may be combined to the first pinion 111 and the second pinion 112, respectively.

More specifically, the first pinion 111 and the second pinion 112 may rotate in the same direction or in the opposite directions by way of the actions of a first wire 125 and a second wire 126 wound around the first pulley 121 and the second pulley 122, respectively. In other words, if the first wire 125 and the second wire 126, respectively, rotate the first pulley 121 and the second pulley 122 in the opposite directions to each other, and further rotate the first pinion 111 and the second pinion 112 in the opposite directions to each other, then the roll gear 106 rotates so that the pincers 101 or the like may operate in the roll direction. However, if the first wire 125 and the second wire 126, respectively, rotate the first pinion 111 and the second pinion 112 in the same direction, then the roll gear 106 does not rotate itself but instead only acts as a component transmitting the force to operate the pincers 101 or the like in the yaw direction.

It will be discussed below how to control the first wire 125 and the second wire 126 to act in the above-mentioned manner.

FIG. 8 is an enlarged view of the handling unit 110 shown in FIG. 6. Further, FIG. 9 is an enlarged view of the roll control unit 145 shown in FIG. 8.

First, reference will be made to FIG. 8.

The handling unit 110 may comprise a yaw control unit 138 connected and fixed to one end of the shaft 130 to control the end effector 100 to operate in the yaw direction; a roll control unit 145 to control the end effector 100 to operate in the roll direction; and a main control unit 159 comprising and supporting the yaw control unit 138 and the roll control unit 145.

The yaw control unit 138 may comprise a main yaw control unit 139 as well as a third pulley 141 and a fourth pulley 142. The main yaw control unit 139 may be connected and fixed to one end of the shaft 130. A rotation axis is inserted in the main yaw control unit 139 to rotate the third pulley 141 and the fourth pulley 142 together with the part of the handling unit 110 except the main yaw control unit 139 (i.e., to act as a fixed axis with respect to the third pulley 141 and the fourth pulley 142 as well as the part of the handling unit 110 except the main yaw control unit 139), and the rotation axis may rotate together with the above components against the main yaw control unit 139. Furthermore, since the first wire 125 and the second wire 126 are wound around the third pulley 141 and the fourth pulley 142, respectively, controlling the main control unit 159 to rotate the third pulley 141 and the fourth pulley 142 in the same direction may cause the operation of the end effector 100 in the yaw direction as described above.

Hereinafter, further reference will be made to FIG. 9.

Meanwhile, the roll control unit 145 may comprise a pair of upper rack gears 146 connected with the first wire 125 to operate in the longitudinal direction; a pair of lower rack gears 147 connected with the second wire 126 to operate in the longitudinal direction; an upper pinion 148 geared between the pair of upper rack gears 146; a lower pinion 149 geared between the pair of lower rack gears 147; and a roll control gear 150 commonly geared to the upper pinion 148 and the lower pinion 149.

The pair of upper rack gears 146 herein is a pair of rack gears geared to both sides of the upper pinion 148 to operate in the opposite directions to each other according to the operation of the upper pinion 148. Further, the pair of lower rack gears 147 is also a pair of rack gears geared to both sides of the lower pinion 149 to operate in the same way. The upper rack gears 146 and the lower rack gears 147 may operate along the rail 151 (Note that the part of the rail 151 for the upper rack gear 146 is not illustrated in FIG. 9 for easier viewing of other components). On the other hand, as shown in FIG. 8, each end of the upper rack gear 146 and the lower rack gear 147 is provided with a control screw 152, to which the first wire 125 or the second wire 126 may be connected. The control screw 152 may function to control the tension of the wires (125, 126).

Meanwhile, the upper pinion 148 and the lower pinion 149 may rotate around an axis disposed in the main control unit 159 (now shown). The roll control gear 150 may be connected to the roll sprocket 155 shown in FIG. 6 (which may be combined to the main control unit 159 to rotate against it) to rotate as the user rotates the roll sprocket 155, such that the upper pinion 148 and the lower pinion 149 may rotate in the opposite directions to each other. Such rotations of the upper pinion 148 and the lower pinion 149 may cause the actions of the pair of the upper rack gears 146 and the pair of the lower rack gears 147 to allow the first wire 125 and the second wire 126 to operate in the opposite directions to each other, which may eventually cause the operation of the end effector 100 in the roll direction as described above.

Furthermore, two pairs of support bars 156, which support the first wire 125 and the second wire 126 between the yaw control unit 138 and the roll control unit 145, respectively, may be further disposed in the main control unit 159. A guide block 157 formed with guide holes 158 to guide the conveyance of the first wire 125 and the second wire 126 toward the roll control unit 145 may be disposed between the support bars 156 and the roll control unit 145. The guide block 157 may be combined to the end of the rail 151.

Meanwhile, the above-mentioned Korean application may be consulted for the components shown in the drawings but not described herein.

Third Embodiment

FIG. 10 shows the overall appearance of a minimally invasive surgical instrument according to yet another embodiment of the invention.

Reference will be made to FIG. 10. The minimally invasive surgical instrument according to the present embodiment may comprise an end effector 100, a handling unit 110, a shaft 130, a first bend 131 and a second bend 132, in the same manner as the first embodiment. The minimally invasive surgical instrument may further comprise a pitch operating unit 160 and a pitch control unit 164 disposed at both ends of the shaft 130 to operate the end effector 100 in the pitch direction. Thus, according to the present embodiment, the end effector 100 may carry out not only the yaw direction, roll direction and/or opening/closing operations but also the pitch direction operation.

The minimally invasive surgical instrument according to the present embodiment is basically configured based on the principles disclosed in the above-mentioned Korean Patent Application No. 2010-115152, while its shaft 130 may include the first bend 131 and the second bend 132 in the same manner as the first embodiment. However, the first bend 131 or the second bend 132 herein does not necessarily need to include the flexible resin.

Further, the minimally invasive surgical instrument according to the present embodiment comprises the similar components for operating the end effector 100 in the yaw or roll direction as described in conjunction with the second embodiment.

There follows the description of FIGS. 6 to 10 (herein, FIGS. 11 to 15) related to the second embodiment disclosed in Korean Application No. 2010-115152, which corresponds to the present embodiment.

FIG. 11 shows an enlarged view of the end effector 100 and the pitch operating unit 160 shown in FIG. 10.

As shown, the pitch operating unit 160 may be disposed between the end effector 100 and the shaft 130 to operate the end effector 100 in the pitch direction. Herein, there may be further provided a plurality of pulleys (161, 162) as illustrated. The actions of such pulleys will be described below.

FIG. 12 shows a lateral view of the pitch operating unit 160 shown in FIG. 11, and FIG. 13 shows a top view of the same.

With reference to FIGS. 11 to 13, the first wire 125 and the second wire 126 may pass through the pitch operating unit 160, and first pitch pulleys 161 and second pitch pulleys 162, which may support the wires, may be provided in the pitch operating unit 160. The (virtual) rotation planes of the pitch pulleys (161, 162) may be substantially orthogonal to the rotation planes of the first pulley 121 and the second pulley 122.

The first wire 125 from the handling unit 110 and the shaft 130 may be wound around the first pulley 121 after passing the upper parts of the second pitch pulleys 162 and then the lower parts of the first pitch pulleys 161, as shown in FIG. 12. Thus, seen from the lateral side of the pitch operating unit 160, the part of the first wire 125 passing the first pitch pulleys 161 and the second pitch pulleys 162 may form an 'X' shape together with the part of the second wire 126 passing and being wound as illustrated, i.e., in the same way as above (Note that such arrangement may be advantageous in maintaining and supporting the tension of the first wire 125 and the second wire 126).

Meanwhile, the first wire 125 may be wound around the first pulley 121 after passing the first and third ones of the plurality of second pitch pulleys 162 and then passing the first and third ones of the plurality of first pitch pulleys 161, as shown in FIG. 13. Further, the second wire 126 may be wound around the second pulley 122 after passing the second and fourth ones of the plurality of second pitch pulleys 162 and then passing the second and fourth ones of the plurality of first pitch pulleys 161, as shown in FIG. 13. Therefore, the first wire 125 and the second wire 126 may be disposed without getting tangled with each other in the pitch operating unit 160, as shown in FIG. 13.

Meanwhile, as shown in FIG. 12, a first pitch wire 163 may be connected and fixed to the side of the pitch operating unit 160 facing the end effector 100 to operate the end effector 100 in the pitch direction. Further, a second pitch wire (not shown) may be connected and fixed to the invisible side of the same part in the same way as the first pitch wire 163 (Note that it is desirable to connect and fix the second pitch wire so that the direction in which the end effector 100 is operated by the second pitch wire (e.g., counterclockwise in FIG. 12) is opposite to the direction in which the end effector 100 is operated by the first pitch wire 163 (e.g., clockwise in FIG. 12)). The second pitch pulleys 162 for the operation of the end effector 100 in the pitch direction may be fixed pulleys (i.e. pulleys fixed on their axes).

FIG. 14 shows a perspective view of the pitch control unit 164 and the yaw control unit 138 shown in FIG. 10, and FIG. 15 shows an exploded perspective view of some components of the same.

Reference will now be made to FIGS. 14 and 15.

As shown in FIG. 15, one end of the first pitch wire 163, the other end of which is connected and fixed to the pitch operating unit 160 as described above, may be connected and fixed to the yaw control unit 138 through the shaft 130 and the pitch control unit 164. In this connection, the pitch control unit 164 may be provided in combination with the yaw control unit 138 as shown in FIG. 14.

More specifically, the first pitch wire 163 from the shaft 130 may be connected and fixed to one part of the yaw control unit 138 (e.g., the part as shown in FIG. 15) after passing third pitch pulleys 166 and fourth pitch pulleys 167, which are included in the pitch control unit 164. Thus, when the user controls the handling unit 110 down in the pitch direction (i.e., clockwise in FIGS. 14 and 15), the first pitch wire 163 is pulled to cause the end effector 100 to operate in the pitch direction as described above. The second pitch wire may be also connected and fixed in the same way as the first pitch wire 163 (Accordingly, when the user controls the handling unit 110 up in the pitch direction (i.e., counterclockwise in FIGS. 14 and 15), the second pitch wire is pulled to cause the end effector 100 to operate in the pitch direction as described above). Herein, the third pitch pulleys 166 may be rotating pulleys to facilitate the conveyance of the first pitch wire 163 and the second pitch wire, and the fourth pitch pulleys 167 may be fixed pulleys that are substantially fixed while the handling unit 110 operates in the pitch direction around a rotation axis (not shown) which may be inserted to the axial hole 169.

Although the present invention has been illustrated in connection with the present embodiment, it is apparent that a person of ordinary skill in the art may modify this embodiment to operate the end effector 100 in the pitch direction by the action of the roll gear 106 and/or in the yaw direction by the action of another yaw operating unit (not shown).

Meanwhile, the above-mentioned Korean application may be consulted for the components shown in the drawings but not described herein.

Fourth Embodiment

FIG. 16 shows the overall appearance of a minimally invasive surgical instrument according to still another embodiment of the invention.

Reference will be made to FIG. 16. The minimally invasive surgical instrument according to the present embodiment may comprise an end effector 200, a handling unit 210, a shaft 250, a first bend 251 and a second bend 252, in the same manner as the first embodiment. The minimally invasive surgical instrument may further comprise a rotation manipulation unit 220 to connect the shaft 250 and the handling unit 210 and to cause joint motion and perform a fixing function, and a joint unit 260 to connect the end effector 200 and the shaft 250 and to carry out joint motion. Thus, according to the present embodiment, the end effector 200 may carry out the pitch direction, yaw direction, roll direction and/or opening/closing operations.

The minimally invasive surgical instrument according to the present embodiment is basically configured based on the principles disclosed in the above-mentioned Korean Patent Application No. 2011-3192, while its shaft 250 may include the first bend 251 and the second bend 252 in the same manner as the first embodiment.

FIG. 44 shows the respective angles from the body of the shaft 250 to one end of the first bend 251 facing the end effector 200 and to the second bend 252 in FIG. 16.

As shown, the angle from the body of the shaft 250 to the end of the first bend 251 facing the end effector 200 may be denoted as α and the angle from the body of the shaft 250 to the second bend 252 may be denoted as β. The specific values of α and β may be selected without limitation by those skilled in the art who implement the minimally invasive surgical instrument according to the present embodiment. However, it may be preferred that the values of α and β be substantially equal to each other so that the roll direction operation of the end effector 200 may not affect the operations of the end effector in the other directions (e.g., the pitch or yaw direction operation). (This may also apply to the other embodiments to be described below.)

FIG. 17 is an exploded view of the first bend 251 of FIG. 16.

Reference will be made to FIG. 17. A first flexible resin 253 may be included within the first bend 251 and connected by means of linear members 256 to the joint unit 260 and a flexible resin in the second bend 252 to be described below. The first flexible resin 253 may transmit the rotation from the handling unit 210 to the end effector 200 so that the end effector 200 may operate in the roll direction almost without any other operations.

FIG. 41 is an enlarged view of the first flexible resin 253 of FIG. 17.

Further reference will be made to FIG. 41. A plurality of via holes as shown may be formed in the first flexible resin 253. The plurality of via holes are provided for a plurality of wires which may hang between the joint unit 260 and a flexible link to be described below, so that the plurality of wires may maintain positions without gathering to one side or getting tangled with each other in the first bend 251.

The end effector 200 and the joint unit 260 of FIG. 17 will be discussed below.

FIG. 18 is an exploded view of the second bend 252 and the rotation manipulation unit 220 of FIG. 16. Further, FIG. 19 is a lateral view of the rotation manipulation unit 220 of FIG. 16.

Reference will be made to FIGS. 18 and 19. A second flexible resin 254 in the second bend 252 may be connected to the first flexible resin 253 by means of the linear members 256 and to a flexible link 215 in the rotation manipulation unit 220 by means of a substantially cylindrical linear member 257 at least a part of which is disposed in the shaft 250. The flexible link 215 may be basically formed in a shape similar to that of the above-described flexible resin, while its size (particularly the diameter of its disk-shaped member) may be greater. Meanwhile, a part of the cylindrical linear member 257 may be surrounded by an annular member 258 in the rotation manipulation unit 220 as illustrated. The annular member 258 may be configured in a form suitable to allow the cylindrical linear member 257 to operate only in the roll direction with respect to a rotating drum 221 belonging to the rotation manipulation unit 220.

When the user manipulates the handling unit 210 in a pitch or yaw direction with respect to the shaft 250, the annular member 258 and the rotating drum 221, the flexible link 215 may be bent in the direction of the manipulation to push or pull the plurality of wires connected between the flexible link 215 and the joint unit 260 so that the end effector 200 eventually operates in the pitch or yaw direction. Further, when the user rotates a roll sprocket 241, the flexible link 215 may transmit the rotation to the second flexible resin 254 by means of the cylindrical linear member 257 and further to the first flexible resin 253 and the end effector 200. That is, the end effector 200 may operate in the roll direction according to the rotation of the roll sprocket 241.

Meanwhile, in order to ensure that the end effector 200 may not operate in the directions other than the roll direction in the above case, a rotating drum fixing member 225 may be further employed to fix the handling unit 210 and the flexible link 215 to the shaft 250, the annular member 258 and the rotating drum 221. Preferably, the rotating drum fixing member 225 may be an annular member comprised of multiple segments, the inner diameter of which may be narrowed when it is fastened by an external force.

FIG. 42 is a detailed diagram of the flexible link 215 and the annular member 258 of FIG. 18. Referring further to FIG. 42, a plurality of via holes may be formed in the flexible link 215, and a plurality of wires that may connect the flexible link 215 and the joint unit 260 may penetrate and bind to the via holes. It may be preferred that the pattern in which the via holes are formed be similar to the via hole pattern on the gyro wheel described in Korean Patent Application No. 2011-3192. Meanwhile, a plurality of via holes may also be formed in the annular member 258 as shown so that the plurality of wires connected between the flexible link 215 and the joint unit 260 may not gather to one side or get tangled with each other. The annular member 258 may also prevent the wires from being caught in the other components of the rotation manipulation unit 220.

However, in the present embodiment, the wires may be connected between the flexible link 215 and the joint unit 260 so that they penetrate the via holes of the annular member 258 without penetrating the cylindrical linear member 257 in the shaft 250, the second flexible resin 254, the linear members 256 and/or the first flexible resin 253.

The embodiments disclosed in Korean application No. 2011-3192 may be consulted for the configurations of the various components that have not been described in detail in connection with the present embodiment, e.g. the configurations of the end effector 200, the handling unit 210, the joint unit 260 and the like, the means for fixing the handling unit 210, or the manner in which the plurality of wires are connected.

Fifth Embodiment

FIG. 20 shows the overall appearance of a minimally invasive surgical instrument according to still yet another embodiment of the invention. Prior to the description of the present embodiment, it should be noted that the reference numerals n and n' herein may denote the components totally different from each other.

The minimally invasive surgical instrument according to the present embodiment may comprise an end effector 100', a handling unit 110', a shaft 150', a first bend C1 and a second bend C2, in the same manner as the first embodiment. The minimally invasive surgical instrument may further comprise a rotation manipulation unit 120' to connect the shaft 150' and the handling unit 110' and to cause joint motion and perform a fixing function, and a joint unit 160' to connect the end effector 100' and the shaft 150' and to carry out joint motion. Thus, according to the present embodiment, the end effector 100' may carry out the pitch direction, yaw direction, roll direction and/or opening/closing operations.

The minimally invasive surgical instrument according to the present embodiment is basically configured based on the principles disclosed in the above-mentioned Korean Patent Application No. 2011-3192, while its shaft 150' may include the first bend C1 and the second bend C2 in the same manner as the first embodiment. The first bend C1 and the second bend C2 may function to transmit the torque caused by the user rotating the roll sprocket 141' to the end effector 100' via the shaft 150' by means of a first flexible resin (not shown) and a second flexible resin (not shown) that respectively constitute the first and second bends.

It is apparent that the first and second flexible resins of the present embodiment may also include a plurality of via holes for a plurality of wires as shown in FIG. 41.

There follows the description of FIGS. 2 to 21 (herein, FIGS. 21 to 40) related to the embodiments disclosed in Korean Application No. 2011-3192, which correspond to the present embodiment.

FIG. 21 is an exploded view of some components of FIG. 20. FIG. 21 shows main elements of the end effector 100' and the joint unit 160' according to one embodiment of the invention.

The end effector 100' may comprise pincers 101' (also referred to as "holder") to operate to hold objects such as surgical instruments; an X-shaped bellows link 105' being connected to one end of the pincers 101' to operate the pincers 101' to carry out expansion and contraction motion; and a support tube 106' being connected to the joint unit 160' to support and operate the bellows link 105'. The support tube 106 may comprise a spring (not shown) to operate the bellows link 105', as necessary.

Meanwhile, the joint unit 160' may comprise a first connecting unit 171' and a second connecting unit 172' for connection to the shaft 150' and the end effector 100', as well as a first joint link 181', a second joint link 182' and a third joint link 183' being sequentially disposed therebetween. This will be discussed below in more detail.

FIG. 22 is a lateral view of the end effector 100' according to one embodiment of the invention, which is shown partially transparently. (That is, there is shown transparently in the figure the interior of a housing to enclose the bellows link 105' and the support tube 106' so that the minimally invasive surgical instrument of the present invention may be used inside the body. It should be understood that even though not explicitly indicated, other elements may also be enclosed with such a housing, as necessary.) When opening/closing wires (not shown), which may be disposed between the end effector 100' and the handling unit 110', apply force to the bellows link 105' to expand it according to the user's manipulation of the handling unit 110', the bellows link 105' may expand from the default state as shown in FIG. 22 to close the pincers 101'. (That is, the pincers 101' may pick up a surgical instrument or the like.) However, when such force is not applied to the bellows link 105', it contracts to open the pincers 101' by virtue of the restitution force of the spring as described above. (That is, the pincers 101' holding a surgical instrument or the like may release it.) Of course, the pincers 101' may be configured to close by default and otherwise open, as desired by those skilled in the art.

FIG. 23 shows lateral and perspective views of the joint link according to one embodiment of the invention. FIG. 24 is an exploded view of the joint unit 160' according to one embodiment of the invention. Further, FIG. 25 shows a plurality of wires P-W1, Y-W1, P-W2 and Y-W2 arranged in the joint unit 160' shown in FIG. 24.

As described above and shown in FIGS. 23 to 25, the joint unit 160' may comprise a first connecting unit 171' and a second connecting unit 172' as well as a first joint link 181', a second joint link 182' and a third joint link 183'. The joint link may comprise a plurality of via holes 161' to provide penetration passages for the wires P-W1, Y-W1, P-W2 or Y-W2 (the via holes may be paired with each other); a slope 165' to facilitate joint motion of the joint unit 160'; and a rotating link 166' to provide rotatable connections between the joint links or between the connecting units and the joint links (the pivot for the rotating link 166' is not shown for convenience).

As shown in FIG. 23, two pairs of rotating links 166' belonging to a joint link may be disposed at both sides of the joint link, respectively. In this case, one pair of rotating links 166' may be oriented substantially perpendicular to the other pair of rotating links 166'. Due to this configuration, the joint unit 160' may comprise joints for pitch direction operation of the end effector 100' (referred to as 'P') and joints for its yaw direction operation (referred to as 'Y') in the order of P-Y-P-Y (or Y-P-Y-P). In order to facilitate joint motion, a joint link may have a groove around its pair of rotating links 166', which is intended for a pair of rotating links 166' of another joint link (or connecting unit) engaged therewith.

Although the specific configuration of the joint links may be modified without limitation as desired by those skilled in the art, a plurality of via holes 161' may preferably be disposed close to the circumference of a joint link so that the torque applied to the joint link by the wires P-W1, Y-W1, P-W2 or Y-W2 passing through the via holes 161' (to be described below) may be as large as possible. In this case, the above-described rotating link 166' may be disposed close to the center of the joint link to suffer less interference from the wires P-W1, Y-W1, P-W2 or Y-W2.

Referring to FIG. 25 in conjunction with FIG. 24, it may be seen that each of a plurality of wires P-W1, Y-W1, P-W2 and Y-W2 for joint motion in the joint unit 160' may extend from the shaft 150' through the via holes 161' of the first connecting unit 171' to the first joint link 181', the second joint link 182', the third joint link 183', or the second connecting unit 172'. It is apparent that the wires P-W1, Y-W1, P-W2 or Y-W2 may hang in the first joint link 181', the second joint link 182', the third joint link 183', or the second connecting unit 172' through the corresponding via holes. More wires of the same types as the plurality of wires P-W1, Y-W1, P-W2 and Y-W2 may also hang, all of which are not shown in FIG. 25.

FIGS. 26 and 27 show the interior of the rotation manipulation unit 120' according to one embodiment of the invention. Further, FIG. 28 shows how joint motion is carried out in the joint unit 160' by a gyro link 115' of the rotation manipulation unit 120' according to one embodiment of the invention.

First, the rotation angle of a yaw joint (i.e., a joint for yaw direction operation of the end effector 100', being formed between the first joint link 181' and the second joint link 182') will be referred to as YA1, where the joint motion of the yaw joint is carried out by the wire Y-W1. Further, the rotation angle of another yaw joint (i.e., a joint for yaw direction operation of the end effector 100', being formed between the third joint link 183' and the second connecting unit 172') will be referred to as YA2, where the joint motion of the yaw joint is carried out by the wire Y-W2.

As shown in FIGS. 25 to 27, the wire Y-W1 extending to the second joint link 182' may connect to the inner one of the via holes of the gyro link 115' to be described below. Further, the wire Y-W2 extending to the second connecting unit 172' may connect to the outer one of the via holes of the gyro link 115'. In this case, the distance between the inner via hole and the center of the gyro link 115' may be denoted as r1, and the distance between the outer via hole and the center of the gyro link 115' may be denoted as r2, as shown in FIG. 28.

According to the above-described configuration, if the user manipulates the handling unit 110' in the yaw direction by some angle (that is, the gyro wheel of the gyro link 115' operates in the yaw direction by some angle), thereby operating the end effector 100' in the yaw direction by the angle, then the relationship between the above-described variables may be approximately established as YA1:YA2=r1:(r2−r1). (In case of the pitch direction operation, the relationship may also be established as PA1:PA2=r1:(r2−r1).) Therefore, in implementing the minimally invasive surgical instrument according to the present invention, those skilled in the art may adjust the ratio of r1:r2 as necessary, thereby determining the distribution of the rotation angles in the joint unit 160' when the end effector 100' operates in the yaw or pitch direction. Preferably, those skilled in the art may determine the ratio of r1:r2=1:2 such that the ratio of YA1:YA2 and PA1:PA2 is about 1:1. Meanwhile, it should be noted that even when the ratio of r1:r2 changes variably, the value of YA1+Ya2 or PA1+PA2, i.e., the angle by which the end effector 100' eventually operates in the yaw or pitch direction, may be substantially constant if the handling unit 110' has been manipulated by a constant angle.

FIG. 29 shows the joint unit 160' in which the joint motion has been carried out according to one embodiment of the invention. As shown in FIG. 29, the first connecting unit 171' possibly abutting the first joint link 181' and the second connecting unit 172' possibly abutting the third joint link 183' may be respectively connected to the first joint link 181' and the third joint link 183' by the rotating links 166', where a slope similar to the slope 165' of the joint link may be included in the corresponding side. The rotation angle of the joint unit 160' in the pitch and yaw directions may preferably range from +90 degrees to −90 degrees. In this case, the inclination angle between the connecting unit and the slope 165' of the joint link may be uniform at 22.5 degrees.

FIG. 30 is a detailed diagram of the rotation manipulation unit 120' according to one embodiment of the invention.

As shown in FIG. 30, the rotation manipulation unit 120' may comprise a gyro link 115', which may carry out gyroscopic motion while being connected to a plurality of wires P-W1, Y-W1, P-W2 and Y-W2 as described above, as well as rotating drums 121' and 122' or the like.

First, the plurality of wires P-W1, Y-W1, P-W2 and Y-W2 may hang in the gyro wheel of the gyro link 115'. (To this end, the gyro wheel of the gyro link 115' may also have a plurality of (inner and outer) via holes.) Accordingly, in using the minimally invasive surgical instrument according to the present invention, the user may fix the shaft 150' at the position of a trocar or the like and then grab the handling unit 110' to operate the handing unit 110 in the pitch or yaw direction against the shaft 150' (i.e., to operate the gyro wheel of the gyro link 115' in the pitch or yaw direction against the shaft 150') so that the wires P-W1, Y-W1, P-W2 or Y-W2 may be generally pushed or pulled to allow joint motion for the end effector 100' to be carried out in the joint unit 160'. Meanwhile, a penetration link 116' may be further disposed in the rotation manipulation unit 120' to provide intermediate penetration passages for the plurality of wires P-W1, Y-W1, P-W2 and Y-W2.

Next, the other elements of the rotation manipulation unit 120' will be discussed below. The rotation manipulation unit 120' may primarily comprise an external rotating drum 121' and an internal rotating drum 122', and the internal rotating drum 122' contains the gyro link 115' and the penetration link 116' therein and may operate only in the roll direction against the external rotating drum 121'. Usually, the handling unit 110' may operate in the pitch or yaw direction against the external rotating drum 121' and the internal rotating drum 122' according to the user's manipulation of the handling unit 110' (that is, the gyro wheel of the gyro link 115' may operate in the pitch or yaw direction against the external rotating drum 121' and the internal rotating drum 122'), which may lead to joint motion in the joint unit 160'. However, when the user activates a rotating drum fixing means 130', a rotating drum fixing member 125' (preferably an annular member comprised of multiple segments) surrounding the external rotating drum 121' may be fastened to fix the handling unit 110' to the external rotating drum 121' and thus prevent any (subsequent) joint motion in the joint unit 160'.

Further reference will be made to FIG. 31. FIG. 31 shows a sequence of the rolling operation of the end effector 100' according to one embodiment of the invention. It should be noted that the bends (C1 or C2) are formed at the positions marked with the tildes in FIG. 31.

As shown in FIG. 31 and described below, the handling unit 110' may be provided with a roll sprocket 141'. When the user rotates the roll sprocket 141', the gyro wheel of the gyro link 115' may operate together in the roll direction. This leads to the roll direction operations of the internal rotating drum 122' (directly connected with the gyro link 115') and the shaft 150' fixed thereto, which eventually results in the roll direction operation of the end effector 100'.

In the above case, the handling unit 110' and the external rotating drum 121' may be fixed to each other as described above, and under such conditions the joint motion in the joint unit 160' of the end effector 100' may be restricted while the roll direction operation of the plurality of wires P-W1, Y-W1, P-W2 and Y-W2 hung in the gyro link 115' may be unrestricted. Therefore, the roll direction operation of the wires P-W1, Y-W1, P-W2 and Y-W2 causes their changed tension to act in the joint unit 160' (as well as to act in consonance with the roll direction operation of the shaft 150') such that the end effector 100' may operate in the roll direction as shown in FIG. 31 while maintaining the joint motion state in the joint unit 160'.

With regard to the arrangements and connections of the above-described elements, further reference will be made to FIGS. 32 to 34. FIG. 32 is an exploded view of the rotation manipulation unit 120' according to one embodiment of the invention. FIG. 33 is an exploded view of the gyro link 115' according to one embodiment of the invention. Further, FIG. 34 shows a specific example of a configuration to fix the handling unit 110' to the external rotating drum 121' according to one embodiment of the invention.

As shown in FIG. 32, one end of the internal rotating drum 122' is engaged with the angular end of the shaft 150'. Thus, when the internal rotating drum 122' rotates in the roll direction, the shaft 150' may operate together in the roll direction. A part of the internal rotating drum 122' may be contained in the external rotating drum 121', as illustrated. Accordingly, the internal rotating drum 122' may only carry out the roll direction operation independently from the external rotating drum 121. As illustrated, the rotating drum fixing member 125' connected to the handling unit 110' may be an annular member comprised of multiple segments and thus may be easily fastened. As the rotating drum fixing member 125' is fastened, the handling unit 110' may be fixed to the external rotating drum 121'. Referring further to FIG. 34, the internal diameter of a rotating drum fixing ring 131' surrounding the rotating drum fixing member 125' may be reduced by a rotating drum fixing pin 132', which is operated according to the manipulation in the handling unit 110' as described below. Therefore, it may be easily understood how the handling unit 110' and the external rotating drum 121' are fixed to each other.

Further, as shown in FIG. 33, the gyro link 115', particularly its gyro wheel, is connected to the roll sprocket 141' and thus may operate in the roll direction according to the rotation of the roll sprocket 141'.

FIG. 35 shows the interior of the handling unit 110' according to one embodiment of the invention. In addition to the above-described rotating drum fixing pin 132' and roll sprocket 141', main elements of the handling unit 110' are shown in FIG. 35. Examples of the main elements may include an opening/closing handle 142' to control the opening/closing of the end effector 100'; a latch gear 143' to convert the rotational motion of the opening/closing handle 142' to the forward and backward motion of opening/closing wires (and preferably to fix the opening/closing control state of the opening/closing handle 142'); a fixing handle 145' to control the forward and backward motion (or the pin loosening/fastening motion) of the rotating drum fixing pin 132'; and a sliding member 146' to convert the rotational motion of the fixing handle 145' to the forward and backward motion of the rotating drum fixing pin 132'. There may be further provided an auxiliary handle 148' to restrict the rotational motion of the fixing handle 145' as necessary and firmly maintain the fixing of the handling unit and the external rotating drum as describe above.

When using the minimally invasive surgery instrument according to the above-described embodiments of the invention, the user may manipulate the handling unit 110' against the shaft 150' so that the end effector 100' carries out joint motion and is disposed at a surgery site; fix the handling unit 110' to the external rotating drum 121' to fix the above state of the joint motion; and rotate the roll sprocket 141' to roll the end effector 100'. Therefore, the user may perform surgical actions (e.g., suturing by a round needle) on the surgical site delicately and conveniently.

FIGS. 36-38 show the connection between the roll sprocket 141' and the opening/closing handle 142' according to one embodiment of the invention. FIG. 36 is an exploded view showing the connection between the roll sprocket 141' and the opening/closing handle 142' according to one embodiment of the invention. Further, FIGS. 37 and 38 are enlarged perspective views of the above connection.

As illustrated, the roll sprocket 141' and the opening/closing handle 142' may be connected via a ferrule insertion tube 192', a screw 193', a hinge 194' and the like. The ferrule insertion tube 192' is provided with a ferrule insertion hole 195' to which the ferrule of the opening/closing wire may be inserted and fixed. The screw 193' may be coupled to the ferrule insertion tube 192' in a manner of fastening/loosening the screw 193'. In this case, the combined length of the ferrule insertion tube 192' and the screw 193' may vary as the number of fastening/loosening the screw 193'. Thus, the user may adjust the combined length of the ferrule insertion tube 192' and the screw 193' before performing a surgery to set the tension of the opening/closing wire as necessary. Meanwhile, the hinge 194' may act together with or independently from the above-described latch gear 143' to convert the rotational motion of the opening/closing handle 142' to the forward and backward motion of the opening/closing wire.

FIG. 39 shows the interior of a rotation manipulation unit 220' according to another embodiment of the invention.

The configuration of the rotation manipulation unit 120' according to one embodiment of the invention has been discussed above with reference to FIG. 32 and the like. In the following, the configuration of the rotation manipulation unit 220' according to another embodiment of the invention will be discussed with reference to FIG. 39. The elements of the rotation manipulation unit 220' similar to those of the rotation manipulation unit 120' will not be described in detail.

The rotation manipulation unit 220' may comprise an external rotating drum 221'; an internal rotating drum 222'; a first rotating drum fixing member 225' to fix to the external rotating drum 221' by acting together with a second rotating drum fixing member 227' to be described below; the second rotating drum fixing member 227' to fix to the external rotating drum 221' by being inserted in a space between the external rotating drum 221' and the first rotating drum fixing member 225' and pressed by the first rotating drum fixing member 225'; and a rotating drum fixing means 230' to insert the second rotating drum fixing member 227' in the space by moving forward the second rotating drum fixing member 227' from its default position.

More specifically, the front end 226' of the first rotating drum fixing member 225' may be fixed to or released from the external rotating drum 221'. Thus, in each case, the handling unit 110' may be fixed to or released from the external rotating drum 221', and further fixed to or released from the shaft 150'. To this end, the frond end 226' may be comprised of an elastic body spaced apart from the external rotating drum 221' at an interval from its default state.

Further, the second rotating drum fixing member 227' may be an annular member that may be pushed by a fixing screw 231' to carry out forward motion as the fixing screw 231' is fastened. When the second rotating drum fixing member 227' is not pushed by the fixing screw 231', it may carry out backward motion to return to its default position by the action of the first rotating drum fixing member 225', particularly by the action of the front end 226'.

Meanwhile, the rotating drum fixing means 230' may comprise the fixing screw 231' having a shape to move forward the second rotating drum fixing member 227' as the fixing screw 231' is disposed at the handling unit 110' and fastened; and connecting members 235' and 236' being eccentrically connected to the head 232' of the fixing screw 231' to operate according to the rotational motion of the fixing handle (not shown), thereby rotating the fixing screw 231'.

FIG. 40 is a diagram of a rotation manipulation unit 220' according to yet another embodiment of the invention. The rotation manipulation unit 220' shown in FIG. 40 is configured to achieve the fixing to the external rotating drum 221' in a manner different from that of the rotation manipulation unit 220' shown in FIG. 39.

The rotation manipulation unit 220' may comprise an external rotating drum 221'; an internal rotating drum 222'; a pressure drum 250' surrounding the external rotating drum 221' to apply pressure to the external rotating drum 221' to achieve the fixing thereto; a pushing plate 255' to push the pressure drum 250' to the external rotating drum 221'; and connecting members 256', 257' and 258' being connected to the lower end of the pushing plate 255' to rotate and push the pushing plate 255' according to some manipulation.

According to the above configuration, the connecting members 256', 257' and 258' may be manipulated to sequentially act to move the lower end of the pushing plate 255' in the direction opposite to the end effector 100' and the upper end of the pushing plate 255' in the direction of the end effector 100'. When the upper end of the pushing plate 255' pushes the pressure drum 250' in the direction of the end effector 100', the pressure drum 250' surrounding the external rotating drum 221' may apply pressure to the external rotating drum 221' to achieve the fixing thereto.

Meanwhile, when the pushing plate 255' moves contrary to the above, the pressure applied to the external rotating drum 221' by the pressure drum 250' is released so that the fixing to the external rotating drum 221' may also be eventually released.

Meanwhile, the above-mentioned Korean application may be consulted for the components shown in the drawings but not described herein.

Sixth Embodiment

FIG. 43 shows the interior of a rotation manipulation unit 120' of a minimally invasive surgical instrument according to still another embodiment of the invention. The components of the present embodiment which are not shown in the drawings may be considered to correspond to their counterparts of the fifth embodiment.

Reference will be made to FIG. 43. In the present embodiment, unlike the fifth embodiment, a part of the external rotating drum 121' extends to fix to the shaft 150' while the internal rotating drum 122' may be fixed to the linear members 136' (preferably having a cylindrical shape) which may operate in the roll direction in the shaft 150'. Therefore, when a gyro wheel of the gyro link 115' operates in the roll direction, the shaft 150' does not operate in the roll direction while the internal rotating drum 122' as well as the linear members 136', the second flexible resin (not shown; substantially included within the second bend C2) and the first flexible resin (not shown; substantially included within the first bend C1) connected thereto may operate in the roll direction. As a result, this leads to the roll direction operations of the joint unit 160' and the end effector 100' by means of the connection configuration as described in the fourth or fifth embodiment.

According to an application of the present invention, at least some of the components such as the handling unit 110, 110' or 210 of the minimally invasive surgical instrument may be changed or modified to those suitable to be driven by a motor-based system (not shown) such as a surgical robot, so that the minimally invasive surgical instrument may be configured to be controlled by an automatic (or semi-automatic) manipulation system rather than the user's manual manipulation.

As an example for the first embodiment, an electric motor included in a surgical robot (not shown) may operate the end effector 100 in the roll direction by directly rotating the linear members 136 or the roll sprocket 155.

For another example, the electric motor may control the opening or closing of the end effector 100 by directly pulling the opening/closing wires.

For yet another example, a system may fix the rolling state of the end effector 100 by directly controlling the drive of the electric motor.

As an example for the second or third embodiment, an electric motor included in a surgical robot (not shown) may operate the end effector 100 in the pitch direction by directly pulling the first pitch wire 163 and/or the second pitch wire. Obviously, the electric motor may operate the end effector 100 in the pitch direction by directly controlling the modified handling unit 110 in the pitch direction.

For another example, the electric motor may operate the end effector 100 in the yaw or roll direction by directly pushing and pulling the first wire 125 and/or the second wire 126. Obviously, the electric motor may operate the end effector 100 in the yaw or roll direction by directly controlling the modified handling unit 110 in the yaw direction (alternatively, directly rotating the third pulley 141 and the fourth pulley 142 in the same direction) or directly rotating the roll sprocket 155 (alternatively, directly rotating the roll control gear 150).

For yet another example, the electric motor may control the opening or closing of the pincers 101 by directly pulling the opening/closing wires.

For still another example, a system may fix the joint motion state, rolling state, or opening/closing state of the end effector 100 by directly controlling the drive of the electric motor.

As an example for the fourth to sixth embodiments, an electric motor (not shown) included in a surgical robot may enable the end effector 200 or 100' to carry out joint motion by directly operating the flexible link 215 or the gyro wheel of the gyro link 115' in the pitch or yaw direction. For another example, the electric motor may enable the end effector 200 or 100' to carry out joint motion by directly operating a wheel in the rotation manipulation unit 220 or 120' in the pitch or yaw direction. For yet another example, the electric motor may enable the end effector 200 or 100' to carry out joint motion by directly pulling some of the plurality of wires P-W1, Y-W1, P-W2 and Y-W2. Obviously, the electric motor may enable the end effector 200 or 100' to carry out joint motion by directly manipulating the modified handling unit 210 or 110'.

For another example, the electric motor may enable the end effector 200 or 100' to operate in the roll direction by directly rotating the flexible link 215, the gyro wheel of the gyro link 115', or the roll sprocket 141'.

For yet another example, the electric motor may control the opening or closing of the pincers 201 or 101' by directly pulling the opening/closing wires.

For still another example, a system may fix the joint motion state, rolling state, or opening/closing state of the end effector 200 or 100' by directly controlling the drive of the electric motor.

Although the present invention has been described in terms of specific items such as detailed elements as well as the limited embodiments and the drawings, they are only provided to help general understanding of the invention, and the present invention is not limited to the above embodiments. It will be appreciated by a person of ordinary skill in the art that various modifications and changes may be made from the above description.

Therefore, the spirit of the present invention shall not be limited to the above-described embodiments, and the entire scope of the appended claims and their equivalents will fall within the scope and spirit of the invention.

What is claimed is:

1. A minimally invasive surgical instrument comprising:
   a shaft;
   an end effector connected to one end of the shaft;
   a joint unit interposed between the shaft and the end effector;
   a plurality of wires connected to the joint unit to enable the end effector to carry out joint motion;
   a handling unit connected to the other end of the shaft; and
   a rotation manipulation unit interposed between the shaft and the handling unit,
   wherein the shaft comprises at least one bend, and the at least one bend includes therein a flexible resin to transmit force to operate the end effector in a roll direction, independently of the shaft;
   the rotation manipulation unit comprises a gyro link, the gyro link being connected with the joint unit by means of the plurality of wires;
   the end effector carries out joint motion by means of the joint unit according to the action of at least some of the plurality of wires caused by a manipulation to the gyro link;
   the joint unit and the gyro link are connected with the flexible resin with a linear member being further interposed therebetween; and
   the rotation manipulation unit further comprises an external rotating drum connected with the shaft, and an internal rotating drum connected with the linear member to operate in the roll direction independently from the external rotating drum.

2. A minimally invasive surgical instrument as claimed in claim 1, wherein the at least one bend comprises a first bend formed in a curved shape on a side of the end effector, and a second bend formed in a shape spreading from the longitudinal central axis of the shaft to the outside.

3. A minimally invasive surgical instrument as claimed in claim 2, wherein the angle from the body of the shaft to one end of the first bend facing the end effector is substantially the same as the angle from the body of the shaft to the second bend.

4. A minimally invasive surgical instrument as claimed in claim 1, wherein a bending member bendable in a pitch direction and a bending member bendable in a yaw direction are alternately arranged in the flexible resin.

5. A minimally invasive surgical instrument as claimed in claim 4, wherein the bending member comprises two disk-shaped members and one connecting member.

6. A minimally invasive surgical instrument as claimed in claim 5, wherein the one connecting member is disposed on a central axis of the two disk-shaped members.

7. A minimally invasive surgical instrument as claimed in claim 1, wherein the linear member is connected with the handling unit.

8. A minimally invasive surgical instrument as claimed in claim 7, wherein the handling unit comprises a roll sprocket, and the linear member is connected with the roll sprocket.

9. A minimally invasive surgical instrument as claimed in claim 1, wherein the plurality of wires are connected through a plurality of via holes included in the flexible resin.

10. A minimally invasive surgical instrument as claimed in claim 1, wherein the plurality of wires are connected through a plurality of via holes included in the gyro link.

* * * * *